(12) United States Patent
Claerebout et al.

(10) Patent No.: US 7,264,812 B2
(45) Date of Patent: Sep. 4, 2007

(54) OSTERTAGIA VACCINE

(75) Inventors: Edwin Claerebout, Lokeren (BE); Peter Geldhof, Merelbeke (BE); Veerle De Maere, Gent (BE); Isabel Vercauteren, Woubrechtegem (BE); Jozef Vercruijsse, Gent (BE)

(73) Assignee: Universiteit Gent, Gent (BE)

( * ) Notice: Subject to any disclaimer, the term of this patent is extended or adjusted under 35 U.S.C. 154(b) by 0 days.

(21) Appl. No.: 10/527,771

(22) PCT Filed: Sep. 11, 2003

(86) PCT No.: PCT/EP03/10189

§ 371 (c)(1),
(2), (4) Date: Mar. 11, 2005

(87) PCT Pub. No.: WO2004/024769

PCT Pub. Date: Mar. 25, 2004

(65) Prior Publication Data

US 2005/0271683 A1    Dec. 8, 2005

(30) Foreign Application Priority Data

Sep. 13, 2002 (US) ............... 10/243,319

(51) Int. Cl.
*A61K 39/00* (2006.01)
(52) U.S. Cl. ................... 424/191.1; 530/855
(58) Field of Classification Search ............. 424/191.1; 530/855
See application file for complete search history.

(56) References Cited

U.S. PATENT DOCUMENTS

| 3,395,218 A * | 7/1968 | Hyman ............... 424/265.1 |
| 6,017,757 A * | 1/2000 | Coyne ............... 435/325 |
| 6,232,086 B1 * | 5/2001 | Pastan et al. ........... 435/7.23 |
| 6,248,329 B1 * | 6/2001 | Chandrashekar et al. 424/191.1 |

FOREIGN PATENT DOCUMENTS

WO     WO95 09182      4/1995

OTHER PUBLICATIONS

Bowie et al, Science, 1990, 247:1306-1310.*
Burgess et al, J. of Cell Bio. 111:2129-2138, 1990.*
Lazar et al., Molecular and Cellular Biology, 1988, 8:1247-1252.*
Bork, Genome Research, 2000, 10:398-400.*
Ellis (Chapter 29 of Vaccines, Plistkin, et al. (eds) WB Saunders, Philadelphia, 1998,pp. 568-575.*
Vercauteren, Isabel et al. "Identification of excretory-secretory products of larval . . . " Molecular and Biochem. Parasitology (Feb. 2003) V126, N2, p. 201-208, XP-001156729.
Chen, Jeng-Shong et al. "Extensive Sequence Conservation Among Insect, Nematode,and . . . " J. of Molecular Evolution (1997) V44, p. 440-451, XP-002264414.
De Maere, V., et al., "Identification of potential protective antigens of Ostertagia ostertagi . . . " Parasitology, Oct. 2002, V 125. p 383-391.
EMBL Database, Mar. 31, 2001, EMBL Database accession No. AJ310819.
EMBL Database, May 14, 2001, EMBL Database accession No. BG733986.
Gencore accession No. AJ310812, Mar. 29, 2001 and Aug. 12, 2001.
Abstract submitted and slides presented during an oral presentation "Identification of protective antigens of *Ostertagia* osterlagi" Moredun Research Inst. (Jul. 2-5, 2002).
Vercauteren, et al. "Isolation and Identification of In Vitro Released Excretory-Secretory Products of . . . " May 04, 2001, Proceedings of meeting of Belgian Society for Parasitology.

* cited by examiner

*Primary Examiner*—Robert A. Zeman
*Assistant Examiner*—Brian Gangle
(74) *Attorney, Agent, or Firm*—Aaron L. Schwartz; William M. Blackstone; Mark W. Milsteed

(57) ABSTRACT

The present invention relates to nucleic acid sequences encoding *Ostertagia ostertagi* proteins and to parts of such nucleic acid sequences that encode an immunogenic fragment of such proteins, and to DNA fragments, recombinant DNA molecules, live recombinant carriers and host cells comprising such nucleic acid sequences or such parts thereof. The invention also relate to *Ostertagia ostertagi* proteins and immunogenic parts thereof encoded by such sequences. Furthermore, the present invention relates to vaccines comprising such nucleic acid sequences and parts thereof, DNA fragments, recombinant DNA molecules, live recombinant carriers and host cells comprising such nucleic acid sequences or such parts thereof, proteins or immunogenic parts thereof and antibodies against such proteins or immunogenic thereof. Also, the inventions relates to the use of said proteins in vaccines and for the manufacture of vaccines. Moreover, the invention relates to the use of aid nucleic acid sequences, proteins or antibodies for diagnostic or vaccination purposes. Finally the invention relates to diagnostic kits comprising such nucleic acids, proteins or antibodies against such proteins.

3 Claims, 11 Drawing Sheets

B

C

A    B    C    D

…

OSTERTAGIA VACCINE

Figure 1:
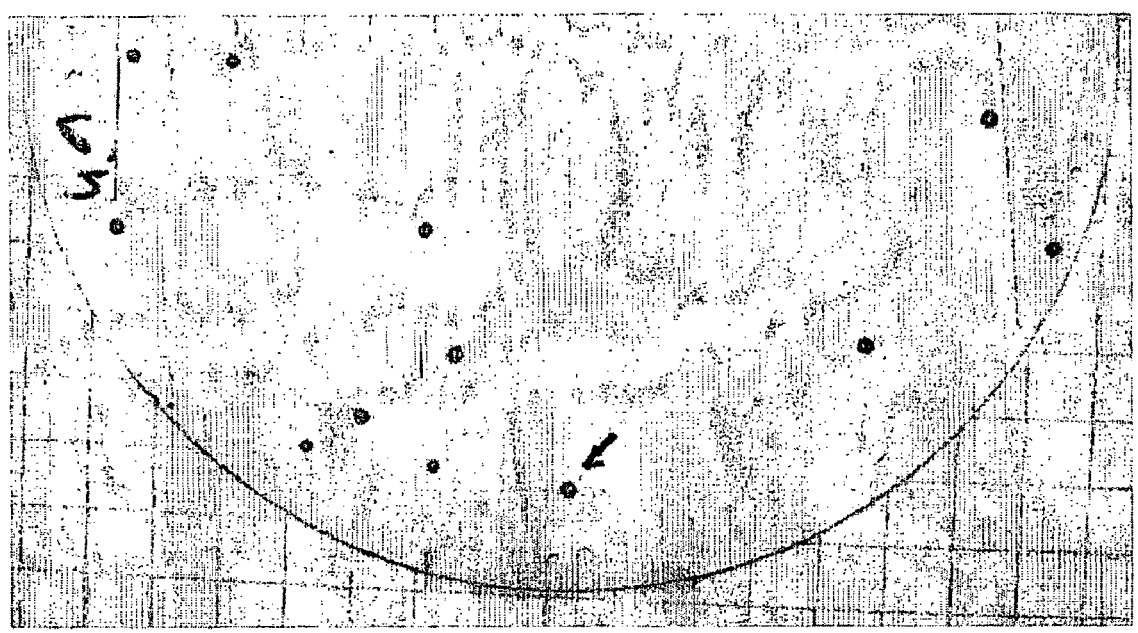

This application is the U.S. National Phase of PCT/EP2003/010189 filed Sep. 11, 2003, which is included herein in its entirety by reference.

The present invention relates to nucleic acid sequences encoding *Ostertagia ostertagi* proteins, to parts of such nucleic acid sequences that encode an immunogenic fragment of such proteins, to DNA fragments, recombinant DNA molecules, live recombinant carriers and host cells comprising such nucleic acid sequences or such parts thereof. The invention also relates to *Ostertagia ostertagi* proteins and immunogenic parts thereof encoded by such sequences. Furthermore, the present invention relates to vaccines comprising such nucleic acid sequences and parts thereof, DNA fragments, recombinant DNA molecules, live recombinant carriers and host cells comprising such nucleic acid sequences or such parts thereof, proteins or immunogenic parts thereof and antibodies against such proteins or immunogenic parts thereof. Also, the invention relates to the use of said proteins in vaccines and for the manufacture of vaccines. Moreover, the invention relates to the use of said nucleic acid sequences, proteins or antibodies for diagnostic or vaccination purposes. Finally the invention relates to diagnostic kits comprising such nucleic acids, proteins or antibodies against such proteins.

There are about 82 million cattle in the EU and about 97 million in the USA most of which are exposed to infection with gastro-intestinal nematodes at grazing, with resultant, often substantial, impaired production efficiency. The most common and most pathogenic of these nematodes is *Ostertagia ostertagi*, which infects the abomasum of cattle. The disease syndrome caused by gastro-intestinal nematodes, commonly referred to as parasitic gastro-enteritis (PGE), drastically diminishes the economic viability of cattle production units (Kloosternan, A. et al., *Parasitology Today* 8, 330-335 (1992); Vercruysse, J. and Claerebout, E., *Veterinary Parasitology* 98, 195-214 (2001)). The animals most at risk for PGE are calves during their first grazing season. Clinical PGE in grazing calves is characterized by (watery) diarrhea, weight loss, a dull hair coat, anorexia, a general loss of condition and eventually death (Anderson, N. et al., *Veterinary Record* 41, 196-204 (1965); Hilderson, H. et al., *Vlaams Diergeneeskundig Tijdschrift* 56, 269-29 (1987)). However, production losses are mainly due to sub-clinical infections, with no overt signs of disease. Substantial reductions in daily weight gain are observed in untreated first grazing season calves with sub-clinical infections (Shaw D. J., et al., *Veterinary Parasitology* 75, 115-131 (1998). Adult cows can still harbor large numbers of *O. ostertagi* (e.g. Borgsteede, F. H. M., et al., *Veterinary Parasitology* 89, 287-296 (2000); Agneessens, J. et al., *Veterinary Parasitology* 90, 83-92 (2000)). Although gastrointestinal nematode infections in adult cows are usually sub clinical, they are associated with decreased levels of milk production (Gross, S. J. et al., *Veterinary Record* 144, 581-587 (1999)). Carcass quality is also affected by gastrointestinal nematode infections, with reduced carcass weight, killing out percentage and related carcass measurements (Entrocasso, C. M. et al., *Research in Veterinary Science* 40, 76-85 (1986)). Control of PGE in Europe is based almost exclusively on the use of anthelmintic drugs (Vercruysse, J. and Dorny, P., *International Journal for Parasitology* 29, 165-175 (1999)). However, the increased use of anthelmintics in cattle over the past two decades (Borgsteede, F. H. M. et al., *Veterinary Parasitology* 78, 23-36 (1998); Schnieder, T. et al., *Veterinary Record* 145, 704-706 (1999); Claerebout, E. et al., *Vlaams Diergeneeskundig Tijdschrift* 69, 108-115 (2000)) has several drawbacks. The high costs of anthelmintic treatments, the negative effect of preventive anthelmintic treatments on the development of natural immunity against gastrointestinal nematodes (Vercruysse, J. et al., *Parasitology Today* 10, 129-132 (1994); Claerebout, E. and Vercruysse J., *Le Point Vétérinaire* (Numéro special) 28, 175-179 (1997)), consumer concerns regarding drug residues in food products and in the environment (Wall, R. and Strong, L., *Nature* 327, 418-421 (1987); Steel, J. W. In: *NRA Special Review of Macrocyclic Lactones*. National Registration Authority for Agricultural and Veterinary Chemicals, Canberra (1998); Strong, L., *Veterinary Parasitology* 48, 3-17 (1993)) and, last but not least, the increasing incidence of parasite resistance against the available anthelmintics (Vermunt, J. J., et al., *Veterinary Record* 137, 43-45 (1995); Vermunt, J. J. et al., *New Zealand Veterinary Journal* 44, 188-193 (1996); Coles, G. C. et al., *Veterinary Record* 142, 255-256 (1998); Gill, J. H. and Lacey, E., *International Journal for Parasitology* 28, 863-877 (1998); and Fiel, C. A. et al., *Revista de Medicina Veterinaria* (Buenos Aires) 81, 310-315 (2000)) are strong incentives for the producers to adopt alternative control systems (Vercruysse & Dorny (1999), supra). Vaccination is being considered as the most feasible solution (Knox, D. P., *Parasitology* 120, S43-S61 (2000)).

However, despite the evolution in biotechnology that allows the development of 'new generation' vaccines based on recombinant DNA technology, no vaccines against gastrointestinal nematode parasites are available until now. The main problems that hamper the development of nematode vaccines in ruminants are (1) most parasite antigens that have been selected for vaccine development are 'hidden antigens', i.e. antigens that are not recognized by the host during a natural infection. Consequently, the immune response that is generated by vaccination with these antigens is not boosted by a natural re-infection; (2) recombinant nematode proteins inducing a protective immune response have so far not been found.

It is an objective of the present invention to provide polypeptides that are capable of contributing to protection against the pathogenic effects of *Ostertagia ostertagi* infection in cattle.

It was now surprisingly found that 7 different polypeptides could be specifically identified and isolated, each of these different polypeptides being capable of inducing an immune response against *Ostertagia* parasites.

The inventors have found that these polypeptides can be used, either alone or in combination with each other, as vaccine components to provide a vaccine, which indeed contributes to the protection against *Ostertagia ostertagi* infection in cattle and helps to decrease the damage caused by *Ostertagia ostertagi*.

Three different approaches have been used for the detection of the genes encoding the vaccine components according to the invention. One approach, presented in detail under Example 1, uses specifically prepared anti-excretory-secretory protein rabbit antiserum for the detection of genes encoding immunoreactive *Ostertagia ostertagi* proteins. This approach has led to the finding of five novel immunogenic proteins for which the coding sequences are depicted in SEQ ID NO: 1, 3, 5, 7 and 9 as given below.

The gene encoding one such protein has now been cloned and sequenced and a nucleic acid sequence of the gene that comprises immunogenic determinants is depicted in SEQ ID NO: 7 The full-length gene encodes a protein of about 1600 amino acids (as partially depicted in SEQ ID NO: 8) with a molecular mass of >=200 kD.

It is well known in the art, that many different nucleic acid sequences can encode one and the same protein. This phenomenon is commonly known as wobble in the second and especially the third base of each triplet encoding an amino acid. This phenomenon can result in a heterology for two nucleic acid sequences still encoding the same protein. Therefore, in principle, two nucleic acid sequences having a sequence homology as low as 70% can still encode one and the same protein.

Thus, one form of a first embodiment of the present invention relates to a nucleic acid sequence encoding an *Ostertagia ostertagi* protein or a part of said nucleic acid sequence that encodes an immunogenic fragment of said protein wherein said nucleic acid sequence or said part thereof has at least 85% homology with the nucleic acid sequence of the *Ostertagia ostertagi* protein gene as depicted in SEQ ID NO: 7

The concept of immunogenic fragments is defined below. The length of a nucleic acid sequence encoding an immunogenic fragment is usually at least 21 nucleotides, but preferably 24, 27, 30, 33 or even 36 nucleotides.

The molecular weight of all proteins according to the invention is determined in gel electrophoresis on a polyacrylamide gel. Due to slight variability of molecular weight determination frequently encountered in the art, the molecular weight can vary. Therefore the molecular weight of the proteins according to the invention should be interpreted as to be its theoretical molecular weight +/–5 kD.

Preferably, a nucleic acid sequence according to the invention encoding this *Ostertagia ostertagi* protein or a part of that nucleic acid sequence that encodes an immunogenic fragment of that protein has at least 90%, preferably 93%, more preferably 95% homology with the nucleic acid sequence of the *Ostertagia ostertagi* protein gene as depicted in SEQ ID NO: 7

Even more preferred is a homology level of 98%, 99% or even 100%.

The level of nucleotide homology can be determined with the computer program "BLAST 2 SEQUENCES" by selecting sub-program: "BLASTN" that can be found at the U.S. Department of Health and Human Services' National Institutes of Health's National Library of Medicine's National Center for Biotechnology Information internet site. A reference for this program is Tatiana A. Tatusova, Thomas L. Madden, FEMS Microbiol. Letters 174, 247-250 (1999). Parameters used are the default parameters: Reward for a match: +1. Penalty for a mismatch: –2. Open gap: 5. Extension gap: 2. Gap x_dropoff: 50.

Nucleotide sequences that are complementary to the sequence depicted in SEQ ID NO: 1, 3, 5, 7, 9, 11 or 13, described herein, or nucleotide sequences that comprise tandem arrays of the sequences according to the invention, are also within the scope of the invention.

Another form of this embodiment relates to a nucleic acid sequence encoding a 28 kD *Ostertagia ostertagi* protein or a part of said nucleic acid sequence that encodes an immunogenic fragment of said protein wherein said nucleic acid sequence or said part thereof has at least 85% homology with the nucleic acid sequence of the *Ostertagia ostertagi* protein gene as depicted in SEQ ID NO: 3.

Preferably, a nucleic acid sequence according to the invention encoding this *Ostertagia ostertagi* protein or a part of that nucleic acid sequence that encodes an immunogenic fragment of that protein has at least 90%, preferably 93%, more preferably 95% homology with the nucleic acid sequence of the *Ostertagia ostertagi* protein gene as depicted in SEQ ID NO: 3.

Even more preferred is a homology level of 98%, 99% or even 100%.

Still another form of this embodiment relates to a nucleic acid sequence encoding a 25 kD *Ostertagia ostertagi* protein or a part of said nucleic acid sequence that encodes an immunogenic fragment of said protein wherein said nucleic acid sequence or said part thereof has at least 85% homology with the nucleic acid sequence of the *Ostertagia ostertagi* protein gene as depicted in SEQ ID NO: 5.

Preferably, a nucleic acid sequence according to the invention encoding this *Ostertagia ostertagi* protein or a part of that nucleic acid sequence that encodes an immunogenic fragment of that protein has at least 90%, preferably 93%, more preferably 95% homology with the nucleic acid sequence of the *Ostertagia ostertagi* protein gene as depicted in SEQ ID NO: 5.

Even more preferred is a homology level of 98%, 99% or even 100%.

Again another form of this embodiment relates to a nucleic acid sequence encoding a 31 kD *Ostertagia ostertagi* protein or a part of said nucleic acid sequence that encodes an immunogenic fragment of said protein wherein said nucleic acid sequence or said part thereof has at least 85% homology with the nucleic acid sequence of the *Ostertagia ostertagi* protein gene as depicted in SEQ ID NO: 1.

Preferably, a nucleic acid sequence according to the invention encoding this 31 kD *Ostertagia ostertagi* protein or a part of that nucleic acid sequence that encodes an immunogenic fragment of that protein has at least 90%, preferably 93%, more preferably 95% homology with the nucleic acid sequence of the *Ostertagia ostertagi* protein gene as depicted in SEQ ID NO: 1.

Even more preferred is a homology level of 98%, 99% or even 100%.

Another form of this embodiment relates to a nucleic acid sequence encoding a 30 kD *Ostertagia ostertagi* protein or a part of said nucleic acid sequence that encodes an immunogenic fragment of said protein wherein said nucleic acid sequence or said part thereof has at least 85% homology with the nucleic acid sequence of the 30 kD *Ostertagia ostertagi* protein gene as depicted in SEQ ID NO: 9.

Preferably, a nucleic acid sequence according to the invention encoding this 30 kD *Ostertagia ostertagi* protein or a part of that nucleic acid sequence that encodes an immunogenic fragment of that protein has at least 90%, preferably 93%, more preferably 95% homology with the nucleic acid sequence of the *Ostertagia ostertagi* protein gene as depicted in SEQ ID NO: 9.

Even more preferred is a homology level of 98%, 99% or even 100%.

A second approach for the detection of vaccine components, presented in detail under Example 2, relied upon the analysis of components in a specific fraction of the parasite, the ES-fraction (excretory-secretory fraction) that play a role in establishing immunity against *Ostertagia ostertagi*. This approach surprisingly led to the finding of the 31 and 30 kD proteins described above (SEQ ID NO: 1 and 9). This provided a full confirmation of the importance of the 31 and 30 kD proteins described above as vaccine components.

A third approach for the detection of vaccine components, presented in detail under Example 3, uses local antibodies obtained from mucus and Antibody Secreting Cell (ASC) culture supernatant. Although serum antibodies can in principle be used to screen for candidate nematode antigens, local antibody responses produced at restricted tissue sites are not always detectable in serum. In addition, the persistence of serum antibodies makes it difficult to differentiate between previous and recent exposures to a pathogen. In contrast, local antibodies from the abomasal draining lymph nodes and from the mucus covering the abomasal mucosa are more specific for antigens present in the infected tissue at the time of examination. It was shown in studies in rats and sheep that cell cultures, containing antibody secreting cells (ASC) induced in vivo in lymph nodes draining the infected tissues, produce antibodies (ASC-probes) in the culture supernatant that specifically reflect the antigen exposure of the draining area and that stage-specific antigens are detected more readily by lymph node ASC-probes than by serum antibodies. Not only the draining lymph nodes but also the covering mucus-layer from the abomasum are a source of local antibodies. After challenge infection of calves with *O. ostertagi*, a negative correlation between fecundity of the worm and parasite specific IgA in the mucus was observed (Claerebout, E. et al., 17th *International Conference of the World Association for the Advancement of Veterinary Parasitology*, Copenhagen, 1999). cDNA libraries of the 3 different parasitic stages were screened with the same antibody probes to identify the nucleotide sequences that code for these antigens.

Details on the isolation of the genes encoding these antigens, and characterization of the protein antigens are presented in Examples 4 and 5.

This highly specific approach has been used for the selection of proteins and genes encoding these proteins that can be directly linked to immune status instead of mere infected status. This approach has surprisingly revealed two more immunogenic proteins, for which the coding sequences are depicted below under SEQ ID NO: 11 and 13.

Therefore, another form of this embodiment relates to a nucleic acid sequence encoding a 24 kD *Ostertagia ostertagi* protein or a part of said nucleic acid sequence that encodes an immunogenic fragment of said protein wherein said nucleic acid sequence or said part thereof has at least 85% homology with the nucleic acid sequence of the *Ostertagia ostertagi* protein gene as depicted in SEQ ID NO: 11.

Preferably, a nucleic acid sequence according to the invention encoding this *Ostertagia ostertagi* protein or a part of that nucleic acid sequence that encodes an immunogenic fragment of that protein has at least 90%, preferably 93%, more preferably 95% homology with the nucleic acid sequence of the 24 kD *Ostertagia ostertagi* protein gene as depicted in SEQ ID NO: 11.

Even more preferred is a homology level of 98%, 99% or even 100%.

Again another form of this embodiment relates to a nucleic acid sequence encoding a 65 kD *Ostertagia ostertagi* protein or a part of said nucleic acid sequence that encodes an immunogenic fragment of said protein wherein said nucleic acid sequence or said part thereof has at least 85% homology with the nucleic acid sequence of the *Ostertagia ostertagi* protein gene as depicted in SEQ ID NO: 13.

Preferably, a nucleic acid sequence according to the invention encoding this *Ostertagia ostertagi* protein or a part of that nucleic acid sequence that encodes an immunogenic fragment of that protein has at least 90%, preferably 93%, more preferably 95% homology with the nucleic acid sequence of the *Ostertagia ostertagi* protein gene as depicted in SEQ ID NO: 13.

Even more preferred is a homology level of 98%, 99% or even 100%.

Since the present invention discloses nucleic acid sequences encoding novel *Ostertagia ostertagi* proteins, it is now for the first time possible to obtain these proteins in sufficient quantities. This can e.g. be done by using expression systems to express the whole or parts of the genes encoding the proteins or immunogenic fragments thereof according to the invention.

Therefore, in a more preferred form of this embodiment, the invention relates to DNA fragments comprising a nucleic acid sequence according to the invention. A DNA fragment is a stretch of nucleotides that functions as a carrier for a nucleic acid sequence according to the invention. Such DNA fragments can e.g. be plasmids, into which a nucleic acid sequence according to the invention is cloned. Such DNA fragments are e.g. useful for enhancing the amount of DNA for use as a primer and for expression of a nucleic acid sequence according to the invention, as described below.

An essential requirement for the expression of the nucleic acid sequence is an adequate promoter functionally linked to the nucleic acid sequence, so that the nucleic acid sequence is under the control of the promoter. It is obvious to those skilled in the art that the choice of a promoter extends to any eukaryotic, prokaryotic or viral promoter capable of directing gene transcription in cells used as host cells for protein expression. Therefore, an even more preferred form of this embodiment relates to a recombinant DNA molecule comprising a DNA fragment and/or a nucleic acid sequence according to the invention wherein the nucleic acid sequence according to the invention is placed under the control of a functionally linked promoter. This can be obtained by means of e.g. standard molecular biology techniques, e.g. Sambrook & Russell: "Molecular cloning: a laboratory manual" (2001), Cold Spring Harbor Laboratory Press; ISBN: 0879695773.

Functionally linked promoters are promoters that are capable of controlling the transcription of the nucleic acid sequences to which they are linked.

Such a promoter can be the native promoter of a novel gene according to the invention or another promoter of *Ostertagia ostertagi*, provided that that promoter is functional in the cells used for expression. It can also be a heterologous promoter. When the host cells are bacteria, useful expression control sequences, which may be used, include the Trp promoter and operator (Goeddel, et al., *Nucl. Acids Res.*, 8, 4057 (1980)); the lac promoter and operator (Chang, et al., *Nature*, 275, 615 (1978)); the outer membrane protein promoter (Nakamura, K. and Inouge, M., *EMBO J.*, 1, 771-775 (1982)); the bacteriophage lambda promoters and operators (Remaut, E. et al., *Nucl. Acids Res.*, 11, 4677-4688 (1983)); the α-amylase (*B. subtilis*) promoter and operator, termination sequences and other expression enhancement and control sequences compatible with the selected host cell.

When the host cell is yeast, useful expression control sequences include, e.g., α-mating factor. For insect cells the polyhedrin or p10 promoters of baculoviruses can be used (Smith, G. E. et al., *Mol. Cell. Biol.* 3, 2156-2165 (1983)). When the host cell is of vertebrate origin illustrative useful expression control sequences include the (human) cytomegalovirus immediate early promoter (Seed, B. et al., *Nature* 329, 840-842 (1987); Fynan, E. F. et al., *PNAS USA* 90, 11478-11482 (1993); Ulmer, J. B. et al., *Science* 259, 1745-1748 (1993)), Rous sarcoma virus LTR (RSV), Gorman, C. M. et al., *PNAS USA* 79, 6777-6781 (1982); Fynan et al., supra; Ulmer et al., supra), the MPSV LTR (Stacey et al., *J. Virology* 50, 725-732 (1984)), SV40 immediate early promoter (Sprague J. et al., *J. Virology* 45, 773 (1983)), the SV-40 promoter (Berman, P. W. et al., *Science* 222, 524-527 (1983)), the metallothionein promoter (Brinster, R. L. et al., *Nature* 296, 39-42 (1982)), the heat shock promoter (Voellmy et al., *PNAS USA* 82, 4949-53 (1985)), the major late promoter of Ad2 and the β-actin promoter (Tang et al., *Nature* 356, 152-154 (1992)). The regulatory sequences may also include terminator and poly-adenylation sequences. Amongst the sequences that can be used are the well known bovine growth hormone poly-adenylation sequence, the SV40 poly-adenylation sequence, the human cytomegalovirus terminator and poly-adenylation sequences.

Bacterial, yeast, fungal, insect and vertebrate cell expression systems are very frequently used systems. Such systems are well known in the art and generally available, e.g. commercially through Clontech Laboratories Inc. (4030 Fabian Way, Palo Alto, Calif. 94303-4607, USA). Next to these expression systems, parasite-based expression systems are attractive expression systems. Such systems are e.g. described in the French Patent Application with Publication number 2 714 074, and in U.S. NTIS Publication No U.S. Ser. No. 08/043,109 (Hoffman, S. and Rogers, W.: Public. Date 1 Dec. 1993).

A very attractive expression system for heterologous nematode gene expression is a nematodal expression system based upon the worm *Caenorrhabditis clegans*. A heterologous expression system for this nematode has been described by Redmond, D. L. et al., in Molecular and Biochemical Parasitology 112, 125-131 (2001). See also Hashmi, S. et al., in Trends in Parasitology 17, 387-393 (2001). The genes according to the present invention can be fused immediately downstream of a *C. elegans* cystein protease promoter, cpr-5, which has been shown recently to direct expression to the gut of *C. elegans* (Redmond et al., 2001) and cloned into the pGEX-vector. The slow growing DR96 unc76(e911) *C. elegans* mutant strain can be transformed by micro-injection of plasmid DNA into the distal arm of the hermaphrodite gonad. The plasmid DNA can e.g. be prepared using the Qiagen method. *Ostertagia* genes according to the invention can be co-injected with the repair plasmid p76-16B. The p76-16B plasmid rescues the unc76 phenotype and allows transformants to be identified through reversion back to the wild type phenotype. Transformed lines in which the second and subsequent generations show the wild type phenotype wilt be maintained. The presence of the injected construct in transgenic worms can easily be verified by PCR analysis of single worms with primers developed specifically for the DNA of interest (Kwa et al., Journal of Molecular Biology 246, 500-510. (1995)). Transgenic worms, rescued by p76-16B, grow more quickly than the unc76(e911) mutants and allow rapid accumulation of transgenic worm material. Because of its rapid life-cycle, transformants can be grown in vitro in large quantities. Somatic extracts of transgenic worms can be prepared by grinding the nematodes in a mortar under liquid nitrogen and resuspending them in 0.05M PBS containing 2% TRI-TONX-100® non-ionic polyethylene glycol octylphenyl ether detergent. Fusion proteins will be purified by affinity chromatography using a Glutathione Sepharose column.

A still even more preferred form of this embodiment of the invention relates to Live Recombinant Carriers (LRCs) comprising a nucleic acid sequence encoding an *Ostertagia ostertagi* protein or an immunogenic fragment thereof according to the invention, a DNA fragment according to the invention or a recombinant DNA molecule according to the invention. These LRCs are microorganisms or viruses in which additional genetic information, in this case a nucleic acid sequence encoding an *Ostertagia ostertagi* protein or an immunogenic fragment thereof according to the invention has been cloned. Cattle infected with such LRCs will produce an immunological response not only against the immunogens of the carrier, but also against the immunogenic parts of the protein(s) for which the genetic code is additionally cloned into the LRC, such as e.g. one or more of the novel *Ostertagia ostertagi* proteins gene according to the invention.

As an example of bacterial LRCs, attenuated *Salmonella* strains known in the art can very attractively be used.

Also, live recombinant carrier parasites have i.a. been described by Vermeulen, A. N. (*Int. J. Parasitol.* 28, 1121-1130 (1998)).

Furthermore, LRC viruses may be used as a way of transporting the nucleic acid sequence into a target cell. Live recombinant carrier viruses are also called vector viruses. Viruses often used as vectors are Vaccinia viruses (Panicali et al; *PNAS USA* 79, 4927 (1982), Herpesviruses (E.P.A. 0473210A2), and Retroviruses (Valerio, D. et al.; in Baum, S. J., Dicke, K. A., Lotzova, E. and Pluznik, D. H. (Eds.), *Experimental Haematology today*—1988. Springer Verlag, New York: pp. 92-99 (1989)).

The technique of in vivo homologous recombination, well known in the art, can be used to introduce a recombinant nucleic acid sequence into the genome of a bacterium, parasite or virus of choice, capable of inducing expression of the inserted nucleic acid sequence according to the invention in the host animal.

Finally another form of this embodiment of the invention relates to a host cell comprising a nucleic acid sequence encoding a protein according to the invention, a DNA fragment comprising such a nucleic acid sequence or a recombinant DNA molecule comprising such a nucleic acid sequence under the control of a functionally linked promoter. This form also relates to a host cell containing a live recombinant carrier comprising a nucleic acid molecule encoding an *Ostertagia ostertagi* protein or an immunogenic fragment thereof according to the invention.

A host cell may be a cell of bacterial origin, e.g. *Escherichia coli, Bacillus subtilis* and *Lactobacillus* species, in combination with bacteria-based plasmids as pBR322, or bacterial expression vectors as the pEX-, pET-, pGEX-series, or with bacteriophages. The host cell may also be of eukaryotic origin, e.g. yeast-cells in combination with yeast-specific vector molecules, or higher eukaryotic cells like insect cells (Luckow et al.; *Bio-technology* 6, 47-55 (1988)) in combination with vectors or recombinant baculoviruses, plant cells in combination with e.g. Ti-plasmid based vectors or plant viral vectors (Barton, K. A. et al.; *Cell* 32, 1033 (1983), mammalian cells like Hela cells, Chinese Hamster Ovary cells (CHO) or Crandell-Rees Feline Kidney-cells, also with appropriate vectors or recombinant viruses.

Also, the host may be a nematode such as *C. elegans*, as explained above.

Another embodiment of the invention relates to the novel *Ostertagia ostertagi* proteins and to immunogenic fragments thereof according to the invention.

The concept of immunogenic fragments will be defined below.

One form of this embodiment relates to an *Ostertagia ostertagi* protein and to immunogenic fragments thereof, wherein the protein or immunogenic fragments have a sequence homology of at least 90%, preferably however 92%, more preferably 94%, 95% or even 96% homology, in that order or preference, to the amino acid sequence as depicted in SEQ ID NO: 8.

Even more preferred is a homology level of 97%, 98%, 99% or even 100% in that order of preference.

The immunogenic fragments of the *Ostertagia ostertagi* protein as depicted in SEQ ID NO: 2, 4, 6, 8, 10, 12 and 14 according to the invention as described herein, preferably have a length of at least 7, more preferably 10, 15, 20, 30 or even 40 amino acids, in that order of preference.

A still even more preferred form of this embodiment relates to this *Ostertagia ostertagi* protein and immunogenic fragments of said protein, encoded by a nucleic acid sequence according to the present invention.

Another form of this embodiment relates to a 28 kD *Ostertagia ostertagi* protein and to immunogenic fragments thereof, wherein the protein or immunogenic fragments have a sequence homology of at least 90%, preferably however 92%, more preferably 94%, 95% or even 96% homology, in that order or preference, to the amino acid sequence as depicted in SEQ ID NO: 4.

Even more preferred is a homology level of 97%, 98%, 99% or even 100% in that order of preference.

A still even more preferred form of this embodiment relates to a 28 kD *Ostertagia ostertagi* protein and immunogenic fragments of said protein, encoded by a nucleic acid sequence according to the present invention.

Still another form of this embodiment relates to a 25 kD *Ostertagia ostertagi* protein and to immunogenic fragments thereof, wherein the protein or immunogenic fragments have a sequence homology of at least 90%, preferably however 92%, more preferably 94%, 95% or even 96% homology, in that order or preference, to the amino acid sequence as depicted in SEQ ID NO: 6.

Even more preferred is a homology level of 97%, 98%, 99% or even 100% in that order of preference.

A still even more preferred form of this embodiment relates to a 25 kD *Ostertagia ostertagi* protein and immunogenic fragments of said protein, encoded by a nucleic acid sequence according to the present invention.

Again another form of this embodiment relates to a 31 kD *Ostertagia ostertagi* protein and to immunogenic fragments thereof, wherein the protein or immunogenic fragments have a sequence homology of at least 90%, preferably however 92%, more preferably 94%, 95% or even 96% homology, in that order or preference, to the amino acid sequence as depicted in SEQ ID NO: 2.

Even more preferred is a homology level of 97%, 98%, 99% or even 100% in that order of preference.

A still even more preferred form of this embodiment relates to a 31 kD *Ostertagia ostertagi* protein and immunogenic fragments of said protein, encoded by a nucleic acid sequence according to the present invention.

One other form of this embodiment relates to a 30 kD *Ostertagia ostertagi* protein and to immunogenic fragments thereof, wherein the protein or immunogenic fragments have a sequence homology of at least 90%, preferably however 92%, more preferably 94%, 95% or even 96% homology, in that order or preference, to the amino acid sequence as depicted in SEQ ID NO: 10.

Even more preferred is a homology level of 97%, 98%, 99% or even 100% in that order of preference.

A still even more preferred form of this embodiment relates to a 30 kD *Ostertagia ostertagi* protein and immunogenic fragments of said protein, encoded by a nucleic acid sequence according to the present invention.

Again an other form of this embodiment relates to a 24 kD *Ostertagia ostertagi* protein and to immunogenic fragments thereof, wherein the protein or immunogenic fragments have a sequence homology of at least 90%, preferably however 92%, more preferably 94%, 95% or even 96% homology, in that order of preference, to the amino acid sequence as depicted in SEQ ID NO: 12.

Even more preferred is a homology level of 97%, 98%, 99% or even 100% in that order of preference.

A still even more preferred form of this embodiment relates to a 24 kD *Ostertagia ostertagi* protein and immunogenic fragments of said protein, encoded by a nucleic acid sequence according to the present invention.

Again another form of this embodiment relates to a 65 kD *Ostertagia ostertagi* protein and to immunogenic fragments thereof, wherein the protein or immunogenic fragments have a sequence homology of at least 90%, preferably however 92%, more preferably 94%, 95% or even 96% homology, in that order or preference, to the amino acid sequence as depicted in SEQ ID NO: 14.

Even more preferred is a homology level of 97%, 98%, 99% or even 100% in that order of preference.

A still even more preferred form of this embodiment relates to a 65 kD *Ostertagia ostertagi* protein and immunogenic fragments of said protein, encoded by a nucleic acid sequence according to the present invention.

The level of protein homology can be determined with the computer program "BLAST 2 SEQUENCES" by selecting sub-program: "BLASTP", that can be found at the U.S. Department of Health and Human Services' National Institutes of Health's National Library of Medicine's National Center for Biotechnology Information internet site. A reference for this program is Tatiana A. Tatusova, Thomas L. Madden, FEMS Microbiol. Letters 174, 247-250 (1999). Matrix used: "blosum62". Parameters used are the default parameters: Open gap: 11. Extension gap: 1. Gap x_dropoff: 50.

It will be understood that, for the particular proteins embraced herein, natural variations can exist between individual *Ostertagia ostertagi* strains. These variations may be demonstrated by (an) amino acid difference(s) in the overall sequence or by deletions, substitutions, insertions, inversions or additions of (an) amino acid(s) in said sequence. Amino acid substitutions which do not essentially alter biological and immunological activities, have been described, e.g. by Neurath et al in *The Proteins*, Academic Press New York (1979). Amino acid replacements between related amino acids or replacements which have occurred frequently in evolution are, inter alia, Ser/Ala, Ser/Gly, Asp/Gly, Asp/Asn, Ile/Val (see Dayhof, M. D., *Atlas of protein sequence and structure*, Nat. Biomed. Res. Found., Washington D.C. (1978), vol. 5, suppl. 3). Other amino acid substitutions include Asp/Glu, Thr/Ser, Ala/Gly, Ala/Thr, Ser/Asn, Ala/Val, Thr/Phe, Ala/Pro, Lys/Arg, Leu/Ile, Leu/Val and Ala/Glu. Based on this information, Lipman and Pearson developed a method for rapid and sensitive protein comparison (*Science* 227, 1435-1441 (1985)) and determining the functional similarity between homologous proteins. Such amino acid substitutions of the exemplary embodiments of this invention, as well as variations having deletions and/or insertions are within the scope of the invention as long as the resulting proteins retain their immune reactivity.

This explains why *Ostertagia ostertagi* proteins according to the invention, when isolated from different field isolates, may have homology levels of about 70%, while still representing the same protein with the same immunological characteristics.

Those variations in the amino acid sequence of a certain protein according to the invention that still provide a protein capable of inducing an immune response against infection with *Ostertagia ostertagi* or at least against the clinical manifestations of the infection are considered as "not essentially influencing the immunogenicity".

When a protein is used for e.g. vaccination purposes or for raising antibodies, it is however not necessary to use the whole protein. It is also possible to use a fragment of that protein that is capable, as such or coupled to a carrier such as e.g. KLH, of inducing an immune response against that protein, a so-called immunogenic fragment. An "immunogenic fragment" is understood to be a fragment of the full-length protein that still has retained its capability to induce an immune response in a vertebrate host, e.g. comprises a B- or T-cell epitope. Shortly, an immunogenic fragment is a fragment that is capable of inducing an antigenic response against an *Ostertagia ostertagi* protein according to the invention. At this moment, a variety of techniques are available to easily identify DNA fragments encoding antigenic fragments (determinants). The method described by Geysen et al. (Patent Application WO 84/03564, Patent Application WO 86/06487, U.S. Pat. No. 4,833,092, *PNAS USA* 81, 3998-4002 (1984), *J. Imm. Meth.* 102, 259-274 (1987), the so-called PEPSCAN method is an easy to perform, quick and well-established method for the detection of epitopes; the immunologically important regions of the protein. The method is used worldwide and as such well known to man skilled in the art. This (empirical) method is especially suitable for the detection of B-cell epitopes. Also, given the sequence of the gene encoding any protein, computer algorithms are able to designate specific protein fragments as the immunologically important epitopes on the basis of their sequential and/or structural agreement with epitopes that are now known. The determination of these regions is based on a combination of the hydrophilicity criteria according to Hopp and Woods (*PNAS USA* 78, 38248-3828 (1981)), and the secondary structure aspects according to Chou and Fasman (*Advances in Enzymology* 47, 45-148 (1987) and U.S. Pat. No. 4,554,101). T-cell epitopes can likewise be predicted from the sequence by computer with the aid of Berzofsky's amphiphilicity criterion (*Science* 235, 1059-1062 (1987) and U.S. Patent Application NTIS U.S. Ser. No. 07/005,885). A condensed overview is found in: Shan Lu, on common principles: *Tibtech* 9, 238-242 (1991); Good et al., on Malaria epitopes: *Science* 235, 1059-1062 (1987); Lu, for a review: *Vaccine* 10, 3-7 (1992); and Berzofsky, for HIV-epitopes: *The FASEB Journal* 5, 2412-2418 (1991). An immunogenic fragment usually has a minimal length of 6, more commonly 7-8 amino acids, preferably more then 8, such as 9, 10, 12, 15 or even 20 or more amino acids. The nucleic acid sequences encoding such a fragment therefore have a length of at least 18, more commonly 24 and preferably 27, 30, 36, 45 or even 60 nucleic acids.

Therefore, one form of still another embodiment of the invention relates to vaccines for combating *Ostertagia ostertagi* infection, that comprise at least one *Ostertagia ostertagi* protein or immunogenic fragments thereof, according to the invention as described above together with a pharmaceutically acceptable carrier.

Still another embodiment of the present invention relates to the *Ostertagia ostertagi* proteins according to the invention or immunogenic fragments thereof for use in a vaccine.

Again another embodiment of the present invention relates to the use of a nucleic acid sequence, a DNA fragment, a recombinant DNA molecule, a live recombinant carrier, a host cell or a protein or an immunogenic fragment thereof according to the invention for the manufacturing of a vaccine, more specifically a vaccine for combating *Ostertagia ostertagi* infection.

One way of making a vaccine according to the invention is by growing the nematode, followed by biochemical purification of an *Ostertagia ostertagi* protein or immunogenic fragments thereof, from the nematode or the supernatant. This is however a very time-consuming way of making the vaccine.

It is therefore much more convenient to use the expression products of a gene encoding an *Ostertagia ostertagi* protein or immunogenic fragments thereof, according to the invention in vaccines. This is possible for the first time now because the nucleic acid sequences of genes encoding 7 novel *Ostertagia ostertagi* proteins suitable as vaccine components is provided in the present invention.

Vaccines based upon the expression products of these genes can easily be made by admixing the protein according to the invention or immunogenic fragments thereof according to the invention with a pharmaceutically acceptable carrier as described below.

Alternatively, a vaccine according to the invention can comprise live recombinant carriers as described above, capable of expressing the protein according to the invention or immunogenic fragments thereof. Such vaccines, e.g. based upon a *Salmonella* carrier or a viral carrier e.g. a Herpesvirus vector have the advantage over subunit vaccines that they better mimic the natural way of infection of *Ostertagia ostertagi*. Moreover, their self-propagation is an advantage since only low amounts of the recombinant carrier are necessary for immunization.

Vaccines can also be based upon host cells as described above that comprise the protein or immunogenic fragments thereof according to the invention.

All vaccines described above contribute to active vaccination, i.e. they trigger the host's defense system.

Alternatively, antibodies can be raised in e.g. rabbits or can be obtained from antibody-producing cell lines as described below. Such antibodies can then be administered to the cow. This method of vaccination, passive vaccination, is the vaccination of choice when an animal is already infected, and there is no time to allow the natural immune response to be triggered. It is also the preferred method for vaccinating animals that are prone to sudden high infection pressure. The administered antibodies against the protein according to the invention or immunogenic fragments thereof can in these cases interfere with *Ostertagia ostertagi*. This approach has the advantage that it decreases or stops *Ostertagia ostertagi* development.

Therefore, one other form of this embodiment of the invention relates to a vaccine for combating *Ostertagia ostertagi* infection that comprises antibodies against an *Ostertagia ostertagi* protein according to the invention or an immunogenic fragment of that protein, and a pharmaceutically acceptable carrier.

Still another embodiment of this invention relates to antibodies against an *Ostertagia ostertagi* protein according to the invention or an immunogenic fragment of that protein.

Methods for large-scale production of antibodies according to the invention are also known in the art. Such methods rely on the cloning of (fragments of) the genetic information encoding the protein according to the invention in a filamentous phage for phage display. Such techniques are described i.a. in review papers by Cortese, R. et al., (1994) in Trends in Biotechn. 12, 262-267, by Clackson, T. & Wells, J. A. (1994) in Trends in Biotechn. 12. 173-183, by Marks, J. D. et al., (1992) in J. Riol. Chem. 267, 16007-16010, by Winter, G. et al., (1994) in Annu. Rev. Immunol. 12, 433-455, and by Little, M. et al., (1994) Biotechn. Adv. 12, 539-555. The phages are subsequently used to screen camelid expression libraries expressing camelid heavy chain antibodies. (Muyldermans, S. and Lauwereys, M., Journ. Molec. Recogn. 12, 131-140 (1999) and Ghahroudi, M. A. et al., FEBS Letters 414, 512-526 (1997)). Cells from the library that express the desired antibodies can be replicated and subsequently be used for large-scale expression of antibodies.

Still another embodiment relates to a method for the preparation of a vaccine according to the invention that comprises the admixing of antibodies according to the invention and a pharmaceutically acceptable carrier.

An alternative and efficient way of vaccination is direct vaccination with DNA encoding the relevant antigen. Direct vaccination with DNA encoding proteins has been successful for many different proteins. (As reviewed in e.g. Donnelly et al., *The Immunologist* 2, 20-26 (1993)). In the field of anti-parasite vaccines, protection against e.g. *Plasmodium yoelii* has been obtained with DNA-vaccination with the *Plasmodium yoelii* circumsporozoite gene (*Vaccine* 12, 1529-1533 (1994)). Protection against *Leishmania major* has been obtained with DNA-vaccination with the *Leishmania major* surface glycoprotein gp63 gene (*Vaccine* 12, 1534-1536 (1994)).

This way of vaccination is also attractive for the vaccination of cattle against *Ostertagia ostertagi* infection. Therefore, still other forms of this embodiment of the invention relate to vaccines comprising nucleic acid sequences encoding a protein according to the invention or immunogenic fragments thereof, vaccines comprising DNA fragments that comprise such nucleic acid sequences or vaccines comprising recombinant DNA molecules according to the invention, and a pharmaceutically acceptable carrier.

Examples of DNA plasmids that are suitable for use in a DNA vaccine according to the invention are conventional cloning or expression plasmids for bacterial, eukaryotic and yeast host cells, many of said plasmids being commercially available. Well-known examples of such plasmids are pBR322 and pcDNA3 (Invitrogen). The DNA fragments or recombinant DNA molecules according to the invention should be able to induce protein expression of the nucleotide sequences. The DNA fragments or recombinant DNA molecules may comprise one or more nucleotide sequences according to the invention. In addition, the DNA fragments or recombinant DNA molecules may comprise other nucleotide sequences such as immune-stimulating oligonucleotides having unmethylated CpG di-nucleotides, or nucleotide sequences that code for other antigenic proteins or adjuvating cytokines.

The nucleotide sequence according to the present invention or the DNA plasmid comprising a nucleotide sequence according to the present invention, preferably operably linked to a transcriptional regulatory sequence, to be used in the vaccine according to the invention can be naked or can be packaged in a delivery system. Suitable delivery systems are lipid vesicles, ISCOMs®, dendromers, niosomes, microparticles, especially chitosan-based microparticles, polysaccharide matrices and the like, (see further below) all well-known in the art. Also very suitable as delivery system are attenuated live bacteria such as *Salmonella* species, and attenuated live viruses such as Herpesvirus vectors, as mentioned above.

Still other forms of this embodiment relate to vaccines comprising recombinant DNA molecules according to the invention.

DNA vaccines can e.g. easily be administered through intradermal application such as by using a needle-less injector. This way of administration delivers the DNA directly into the cells of the animal to be vaccinated. Amounts of DNA in the range between 10 pg and 1000 µg provide good results. Especially if the DNA is self-replicating, minor amounts will suffice. Preferably, amounts in the microgram range between 1 and 100 µg are used.

In a further embodiment, the vaccine according to the present invention additionally comprises one or more antigens derived from cattle pathogenic organisms and viruses, antibodies against those antigens or genetic information encoding such antigens and/or a pharmaceutical component such as an antibiotic.

Of course, such antigens, antibodies against such antigens, or genetic information can be of *Ostertagia ostertagi* origin, such as e.g. another *Ostertagia ostertagi* antigen. It can also be an antigen, antibodies or genetic information selected from another cow pathogenic organism or virus. Such organisms and viruses are preferably selected from the group of Bovine Herpesvirus, Bovine Viral Diarrhea virus, Parainfluenza type 3 virus, Bovine Paramyxovirus, Foot and Mouth Disease virus, *Pasteurella haemolytica*, Bovine Respiratory Syncytial Virus, *Theileria* sp., *Babesia* sp., *Trypanosoma* sp., *Anaplasma* sp., *Neospora caninum*, *Staphylococcus aureus*, *Streptococcus agalactiae*, *Mycoplasma*, *E. coli*, *Enterobacter*, *Klebsiella*, *Citrobacter*, *Cryptosporidium*, *Salmonella* and *Streptococcus dysgalactiae*.

Vaccines based upon one or more of the *Ostertagia ostertagi* proteins according to the invention are also very suitable as marker vaccines. A marker vaccine is a vaccine that allows to discriminate between vaccinated and field-infected cows e.g. on the basis of a characteristic antibody panel, different from the antibody panel induced by wild type infection. A different antibody panel is induced e.g. when an immunogenic protein present on a wild type *Ostertagia* is not present in a vaccine: the host will then not make antibodies against that protein after vaccination. Thus, a vaccine based upon any of the *Ostertagia ostertagi* proteins according to the invention would only induce antibodies against that specific protein, whereas a vaccine based upon a live wild-type, live attenuated or inactivated whole *Ostertagia ostertagi* would induce antibodies against all or most of the nematodal proteins.

A simple ELISA test, having wells comprising any other *Ostertagia* protein except for the *Ostertagia ostertagi* proteins according to the present invention and wells comprising only one or more purified *Ostertagia ostertagi* proteins according to the invention suffices to test serum from cows and to tell if the cows are either vaccinated with the protein vaccine according to the invention or suffered from *Ostertagia ostertagi* field infection.

All vaccines according to the present invention comprise a pharmaceutically acceptable carrier. A pharmaceutically acceptable carrier can be e.g. sterile water or a sterile physiological salt solution. In a more complex form the carrier can e.g. be a buffer.

Methods for the preparation of a vaccine comprise the admixing of a protein or an immunogenic fragment thereof, according to the invention and/or antibodies against that protein or an immunogenic fragment thereof, and/or a nucleic acid sequence and/or a DNA fragment, a recombinant DNA molecule, a live recombinant carrier or host cell according to the invention, and a pharmaceutically acceptable carrier.

Vaccines according to the present invention may in a preferred presentation also contain an immunostimulatory substance, a so-called adjuvant. Adjuvants in general comprise substances that boost the immune response of the host in a non-specific manner. A number of different adjuvants are known in the art. Examples of adjuvants frequently used in cow vaccines are muramyldipeptides, lipopolysacharides, several glucans and glycans and Carbopol® (a homopolymer).

The vaccine may also comprise a so-called "vehicle". A vehicle is a compound to which the protein adheres, without being covalently bound to it. Such vehicles are i.a. bio-microcapsules, micro-alginates, liposomes and macrosols, all known in the art. Microparticles, more specifically those based upon chitosan, especially for use in oral vaccination are very suitable as vaccine vehicles.

A special form of such a vehicle, in which the antigen is partially embedded in the vehicle, is the so-called ISCOM® (EP 109.942, EP 180.564, EP 242.380)

In addition, the vaccine may comprise one or more suitable surface-active compounds or emulsifiers, e.g. Span® or Tween®.

Antigens will preferably be combined with adjuvants that are readily available and that are registered for use in domestic animals, e.g. aluminum hydroxide, a Th2-like modulating adjuvant.

Two alternative approaches for antigen delivery are especially suitable for application of the vaccines according to the present invention:
a. systemic immunization with the inclusion of adjuvantia modulating immune responses towards the mucosa, such as vitamin D3 (Van der Stede, Y., et al., *Vaccine* 19, 1870-1878 (2001)) or QuilA®, and
b. direct delivery to the respiratory mucosa by inhalation of naked DNA (plasmid) (Vanrompay, D., et al., *Immunology* 103, 106-112 (2001)).

Addition of CpG oligonucleotide sequences inside or outside the plasmid is also preferred for improving protection (Van der Stede, Y., et al., *Vet. Immunol. Immunopathol.*, 86, 31-41 (2002).

Often, the vaccine is mixed with stabilizers, e.g. to protect degradation-prone proteins from being degraded, to enhance the shelf-life of the vaccine, or to improve freeze-drying efficiency. Useful stabilizers are i.a. SPGA (Bovarnik et al; *J. Bacteriology* 59, 509 (1950)), carbohydrates e.g. sorbitol, mannitol, trehalose, starch, sucrose, dextran or glucose, proteins such as albumin or casein or degradation products thereof, and buffers, such as alkali metal phosphates.

In addition, the vaccine may be suspended in a physiologically acceptable diluent. It goes without saying, that other ways of adjuvating, adding vehicle compounds or diluents, emulsifying or stabilizing a protein are also embodied in the present invention.

Vaccines according to the invention that are based upon the protein according to the invention or immunogenic fragments thereof can very suitably be administered in amounts ranging between 1 and 100 micrograms of protein per animal, although smaller doses can in principle be used. A dose exceeding 100 micrograms will, although immunologically very suitable, be less attractive for commercial reasons.

Vaccines based upon live attenuated recombinant carriers, such as the LRC-viruses, parasites and bacteria described above can be administered in much lower doses, because they multiply themselves during the infection. Therefore, very suitable amounts would range between $10^3$ and $10^9$ CFU/PFU for both bacteria and viruses.

Vaccines according to the invention can be administered e.g. intradermally, subcutaneously, intramuscularly, intraperitoneally, intravenously, or at mucosal surfaces such as orally or intranasally.

For efficient protection against disease, a quick and correct diagnosis of *Ostertagia ostertagi* infection is important.

Therefore it is another objective of this invention to provide diagnostic tools suitable for the detection of *Ostertagia ostertagi* infection.

The nucleic acid sequences, the proteins and the antibodies according to the invention are also suitable for use in diagnostics.

Therefore, another embodiment of the invention relates to nucleic acid sequences, proteins and antibodies according to the invention for use in diagnostics.

The nucleic acid sequences or fragments thereof according to the invention can be used to detect the presence of *Ostertagia ostertagi* in cows. A sample taken from the abomasums of cows infected with *Ostertagia ostertagi* will comprise nucleic acid material derived from said parasite, including nucleic acid sequences encoding for the protein according to the invention. These nucleic acid sequences will hybridize with a nucleic acid sequence according to the invention. Suitable methods for the detection of nucleic acid sequences that are reactive with the nucleic acid sequences of the present invention include hybridization techniques including but not limited to PCR techniques and NASBA® techniques. Thus the nucleic acid sequences according to the invention can be used to prepare probes and primers for use in PCR and or NASBA techniques.

A diagnostic test kit for the detection of *Ostertagia ostertagi* may e.g. comprise tools to enable the reaction of *Ostertagia* nucleic acid isolated from the cows to be tested with these tools. Such tools are e.g. specific probes or (PCR-) primers, also referred to as primer fragments, based upon the nucleic acid sequences according to the invention. If genetic material of *Ostertagia ostertagi* is present in the animal, this will e.g. specifically bind to specific PCR-primers and, e.g. after cDNA synthesis, will subsequently become amplified in PCR-reaction. The PCR-reaction product can then easily be detected in DNA gel electrophoresis.

Standard PCR-textbooks give methods for determining the length of the primers for selective PCR-reactions with *Ostertagia ostertagi* DNA. Primer fragments with a nucleotide sequence of at least 12 nucleotides are frequently used, but primers of more than 15, more preferably 18 nucleotides are somewhat more selective. Especially primers with a length of at least 20, preferably at least 30 nucleotides are very generally applicable. PCR-techniques are extensively described in C. Dieffenbach & G. Dveksler: *PCR primers: a laboratory manual*, CSHL Press, ISBN 879694473 (1995)).

Nucleic acid sequences according to the invention or primers of those nucleic acid sequences having a length of at least 12, preferably 15, more preferably 18, even more preferably 20, 22, 25, 30, 35 or 40 nucleotides in that order of preference, wherein the nucleic acid sequences or parts thereof have at least 70% homology with the nucleic acid sequence as depicted in SEQ ID NO: 1, 3, 5, 7, 9, 11 or 13 are therefore also part of the invention. Primers are understood to have a length of at least 12 nucleotides and a homology of at least 70%, more preferably 80%, 85%, 90%, 95%, 98%, 99% or even 100%, in that order of preference, with the nucleic acid sequence as depicted in SEQ ID NO:

1, 3, 5, 7, 9, 11 or 13. Such nucleic acid sequences can be used as primer fragments in PCR-reactions in order to enhance the amount of DNA that they encode or in hybridization reactions. This allows the quick amplification or detection on blots of specific nucleotide sequences for use as a diagnostic tool for e.g. the detection of *Ostertagia ostertagi* as indicated above.

Another test on genetic material is based upon *Ostertagia* material obtained from e.g. a swab, followed by classical DNA purification followed by classical hybridization with radioactively or color-labeled primer fragments. Colour-labelled and radioactively labeled fragments are generally called detection means. Both PCR-reactions and hybridization reactions are well-known in the art and are i.a. described in Sambrook & Russell, supra Thus, one embodiment of the invention relates to a diagnostic test kit for the detection of *Ostertagia ostertagi* nucleic acid sequences. Such a test comprises a nucleic acid sequence according to the invention or a primer fragment thereof.

A diagnostic test kit based upon the detection of antigenic material of the specific *Ostertagia ostertagi* proteins according to the invention and therefore suitable for the detection of *Ostertagia ostertagi* infection may i.a. comprise a standard ELISA test. In one example of such a test the walls of the wells of an ELISA plate are coated with antibodies directed against any of the proteins according to the invention. After incubation with the material to be tested, labeled anti-*Ostertagia ostertagi* antibodies are added to the wells. A color reaction then reveals the presence of antigenic material from *Ostertagia ostertagi*. Therefore, still another embodiment of the present invention relates to diagnostic test kits for the detection of antigenic material of *Ostertagia ostertagi*. Such test kits comprise antibodies against a protein according to the invention or a fragment thereof according to the invention.

A diagnostic test kit based upon the detection in serum of antibodies against a protein of *Ostertagia ostertagi* according to the invention and therefore suitable for the detection of *Ostertagia ostertagi* infection may i.a. comprise a standard ELISA test. In such a test the walls of the wells of an ELISA plate can e.g. be coated with an *Ostertagia ostertagi* protein according to the invention. After incubation with the material to be tested, labeled anti-bodies against that protein are added to the wells. A color reaction then reveals the presence of antibodies against *Ostertagia ostertagi*.

Therefore, still another embodiment of the present invention relates to diagnostic test kits for the detection of antibodies against *Ostertagia ostertagi*. Such test kits comprise an *Ostertagia ostertagi* protein according to the invention or a fragment thereof according to the invention.

The design of the immunoassay may vary. For example, the immunoassay may be based upon competition or direct reaction. Furthermore, protocols may use solid supports or may use cellular material. The detection of the antibody-antigen complex may involve the use of labeled antibodies; the labels may be, for example, enzymes, fluorescent-, chemoluminescent-, radio-active- or dye molecules.

Suitable methods for the detection of antibodies reactive with a protein according to the present invention in the sample include the enzyme-linked immunosorbent assay (ELISA), immunofluorescence test (IFT) and Western blot analyses.

The proteins or immunogenic fragments thereof according to the invention e.g. expressed as indicated above can be used to produce antibodies, which may be polyclonal, mono-specific or monoclonal (or derivatives thereof). If polyclonal antibodies are desired, techniques for producing and processing polyclonal sera are well known in the art (e.g. Mayer and Walter, eds. *Immunochemical Methods in Cell and Molecular Biology*, Academic Press, London (1987)).

Monoclonal antibodies, reactive against the protein according to the invention or an immunogenic fragment thereof according to the present invention, can be prepared by immunizing inbred mice by techniques also known in the art (Kohler and Milstein, *Nature*, 256, 495-497 (1975)).

EXAMPLES

Example 1

1.1. Parasite ES Products, EX Products and Anti-ES Rabbit Serum Preparation

EX products were prepared as described in Geldhof, P., et al., *Parasite Immunology* 24, 263-270 (2002). EX used in this example is comparable to S1 as described in this publication. Excretory-secretory products were prepared as described by Geldhof P, et al., *Parasitology* 121, 639-647 (2000). Rabbits were immunized three times, with one week interval, with 100 μg of the obtained $L_3$, $L_4$ and Adult stage ES proteins in combination with Freund's adjuvant and bled three weeks after the last immunization. Polyclonal sera from these rabbits were used for immunoscreening of *O. ostertagi* cDNA libraries.

1.2. *O. ostertagi* cDNA Library Construction

Total RNA of $L_3$, $L_4$ and Adult parasites was prepared using TRIZOL® Reagent (phenol solution available from GibcoBRL, Life Technologies). PolyA$^+$ RNA was purified using mRNA Separator® Kit (Clontech Laboratories, Inc.). Three μg of mRNA was convened into first strand cDNA with random hexamer primers (SuperScript® Choice System for cDNA Synthesis, GibcoBRL, Life Technologies). Double stranded cDNA was modified with EcoRI-NotI adapters and cloned into the lambda gt11 vector (Stratagene). Recombinant lambda phages were packaged (Gigapack®III Gold Packaging Extract, Stratagene) and the packaging reaction was titrated. The $L_3$ cDNA library was estimated to contain $1.15 \times 10^6$ independent clones; the $L_4$ cDNA library $9.6 \times 10^6$ and the Adult cDNA library contained $3.41 \times 10^8$ plaque forming units. Upon amplification these cDNA libraries were immunoscreened with the anti-ES rabbit sera.

1.3. Immunoscreening of cDNA Library

Approximately 100,000 plaques were plated onto Luria Broth agar (8,000 plaques per plate) and replicas were made on nitrocellulose filters soaked in 10 mM isopropylthio-β-D-galactoside. Upon blocking the background (5% milk powder in PBST, Nestlé Gloria) the filters were incubated overnight with rabbit serum, diluted (1:200) in blocking buffer. Goat-anti-rabbit serum coupled to horseradish peroxidase (1:1000 dilution) was used as a conjugate and the antigen-antibody complexes were detected with diaminobenzidine. Reacting plaques were re-screened until a homogeneous population of immunopositive recombinant phages was obtained. Purified plaques were resuspended in sterile SM buffer (50 mM Tris-HCl, pH 7.5, 100 mM NaCl, 10 mM $MgSO_4$) and stored at 4° C.

1.4. Cloning and DNA Sequence Analysis of cDNA Inserts

Phage inserts were PCR amplified with lambda gt11 primers:

```
λgt11F
5'-GGTGGCGACGACTCCTGGAGCCCG-3'    (SEQ ID NO:15)
and

λgt11R
5'-TTGACACCAGACCAACTGGTAATG-3',   (SEQ ID NO:16)
``` and cloned into a plasmid vector (pGEM-T®, Promega). DH5α E. coil transformants containing the recombinant plasmid were selected on Luria Broth agar plates supplemented with 0.1 mg/ml ampicillin, 0.1 mM isopropylthio-β-D-galactoside, and 40 μg/ml 5-bromo-4-chloro-3-indolyl-β-D-galactose and the cDNA inserts were PCR amplified with vector primers:

```
SP6  5'-ATTTAGGTGACACTATAGAA-3'   (SEQ ID NO:17)
and

T7   5'-GTAATACGACTCACTATAGGGC-3'. (SEQ ID NO:18)
```

The nucleotide sequence of the cDNA clones was determined by the dideoxy chain terminator method using fluorescent BigDye™ terminators in a 377 automated DNA sequencer (PE Biosystems). DNA sequence data were assembled (DNASTAR®, Inc.) and compared with nucleic acid (Blast+Beauty) and amino acid sequences (BlastX+Beauty) in various databases (EMBL, GenBank, WU-Blast2 and Swiss-Prot).

Results of Example 1:

The screening method using specifically prepared anti-excretory-secretory rabbit antiserum for the detection of genes encoding immunoreactive Ostertagia ostertagi led to the detection of five novel genes encoding vaccine components.

All five genes were found to be present in the Ostertagia ostertagi Adult stage cDNA library.

1) a gene encoding a novel immunogenic protein was found, of which the nucleotide sequence encoding important immunogenic determinants is given in SEQ ID NO: 7 The gene encodes a protein with a length of about 1600 amino acids and a molecular weight of >=200 kD. The amino acid sequence of an important immunoreactive part of this protein is given in SEQ ID NO: 8. As can be seen in FIG. 1, several clones, one of which is indicated by an arrow, comprise at least parts of the gene that encode an immunogenic part of this protein. It can be clearly seen that this protein is strongly recognized by antibodies against this protein.

2) a gene encoding a novel immunogenic protein of 28 kD was found. Most of the nucleotide sequence of this gene is given in SEQ ID NO: 3. The amino acid sequence of the protein is given in SEQ ID NO: 4. As can be seen in FIG. 2B, in the lane denominated ES and EX (see under 1.1. for explanation) the clear band of about 28 kD representing this protein is strongly recognized by monospecific antisera purified on lanes of plaque pure immunopositive clones encoding the protein.

3) a gene encoding a novel immunogenic protein of 25 kD was found. The nucleotide sequence of this gene is given in SEQ ID NO: 5. The amino acid sequence of the protein is given in SEQ ID NO: 6. As can be seen in FIG. 2C, in the lane denominated EX (see under 1.1. for explanation) the clear band of about 25 kD representing this protein is strongly and highly specifically recognized by monospecific antisera purified on lanes of plaque pure immunopositive clones encoding this protein.

4) a gene encoding a novel immunogenic protein of 31 kD was found. The nucleotide sequence of this gene is given in SEQ ID NO: 1. The amino acid sequence of the protein is given in SEQ ID NO: 2. In FIG. 3B, in the boxed region, the four right-hand proteins are forms of this protein. (See also under results of Example 2). From FIG. 3A it follows that the protein is strongly recognized by monospecific antisera purified on lanes of plaque pure immunopositive clones encoding this protein.

5) a gene encoding a novel immunogenic protein of 30 kD was found The nucleotide sequence of this gene is given in SEQ ID NO: 9. The amino acid sequence of the protein is given in SEQ ID NO: 10. In FIG. 3B in the boxed region, the two left-hand proteins are forms of this protein. (See also under results of Example 2). From FIG. 3A it follows that the protein is strongly recognized by monospecific antisera purified on lanes of plaque pure immunopositive clones encoding this protein.

Example 2

2.1. Preparation of Antigens

Adult O. ostertagi parasites and Adult ES-products were obtained as described by Geldhof et al. (2000, Parasitology, 121, 639-647).

2.2. Chromatography on Thiol-sepharose

Total ES was preincubated with a final concentration of 2.5 mM dithiothreitol (DTT) for 30 minutes at 37° C. prior to chromatography. Excess DTT was removed by passage through a 10×2.6 cm Sephadex® G-25 (Pharmacia) column and eluted with 10 mM Tris, 0.5 M NaCl, pH 7.4 at 5 ml/minute. An activated Thiol-Sepharose 4B (Sigma) column, 5 ml bed volume, was equilibrated in 10 mM Tris, 0.5 M NaCl, pH 7.4. Protein samples (10 mg/run) were applied to the Thiol-Sepharose 4B column at a flow rate of 5 ml/hour. Unbound material was eluted by washing the column with equilibration buffer (10 mM Tris, 0.5 M NaCl, pH 7.4) till the $OD_{280}$ had returned to a steady baseline. Bound material was eluted with equilibration buffer containing 50 mM DTT at a flow rate of 5 ml/hour. The peak fractions were pooled. DTT was removed from the eluted proteins by passage, at 5 ml/minute, through a Sephadex® G-25 (Pharmacia) column in 10 mM Tris pH 7.4. The peak fractions were again pooled and protein content determined by the BCA method (Pierce). Both purifications, S3- and ES-thiol, had a yield between 10 and 15%. Aliquots of the ES-thiol fractions were removed for SDS-PAGE and substrate gel analysis. The remainder of the eluates was then stored at −70° C. until required.

2.3. 1D and 2D Gel Electrophoresis

The peptide components of ES-thiol were visualized by Coomassie Blue staining (0.1% Coomassie Blue R-250 in 40% methanol and 10% acetic acid) following fractionation of 10 μg protein sample by 10% SDS-PAGE under reducing conditions.

The 2D gelelectrophoresis was performed using the 1 PG-SDS/PAGE system according to Bjellqvist et al. (Electrophoresis 14, 1357-1365 (1993)). The protein samples were precipitated by adding 10 volumes of ice-cold acetone and left for 2 hours at −20° C. The acetone was discarded after centrifugation. The pellet was resolved for 2 hours in rehydration solution containing 9 M urea, 4% CHAPS (Pharmacia), Bromophenol Blue, 18 mM dithiothreitol and 2% IPG buffer (Pharmacia). This sample, approximately 100 μg of protein, was loaded on 7 cm Immobiline strips (pH 3-10, Pharmacia) to perform the isoelectric focusing. The strip was subsequently washed for 30 minutes in 50 mM Tris-Cl pH 8.8 containing 6 M Urea, 30% glycerol (v/v), 2% SDS (w/v), 64 mM dithiothreitol and a trace of bromophenol blue. The second dimension was carried out on 12% SDS-PAGE. Gels were stained by Coomassie Colloidal staining (Sigma).

2.4. Western Blotting

The serum antibody responses of the calves to the immunizations with ES-thiol were evaluated by Western blotting using sera harvested one week after the second immunization. Five μg of ES-thiol was fractionated using 10% SDS-PAGE under reducing conditions and then blot transferred onto a PVDF membrane. The blot sections were cut into strips and blocked overnight in 10% horse serum in PBST. After 2 hours of probing with pooled sera (diluted 1:400 in 2% horse serum in PBST) from the different groups the conjugate (Rabbit anti-bovine-HPRO, Sigma, 1:8000 in 2% horse serum in PBST) was added for one hour. Recognized antigens were visualized by adding 0.05% 3,3-diaminobenzidine tetrachloride in PBS containing 0.01% $H_2O_2$ (v/v).

2.5. Mass Spectrometric Analysis

The mass spectrometric analysis was performed essentially as previously reviewed Jensen et al. (*Proteins*, Suppl 2, 74-89 (1998)). In short, protein spots were in-gel digested using trypsin and the peptides were subsequently purified with the AnchorChip® technology. The peptide samples were analyzed by MALDI-TOF mass spectrometry. Remaining material was used for a LC-MS/MS analysis to determine the amino acid sequence of the different peptides.

Results of Example 2:

Peptide Profile of ES-Thiol and Complete ES

Figure 3:
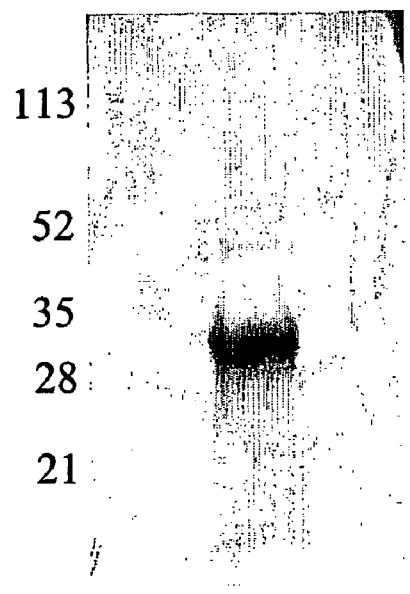
Figure 3:
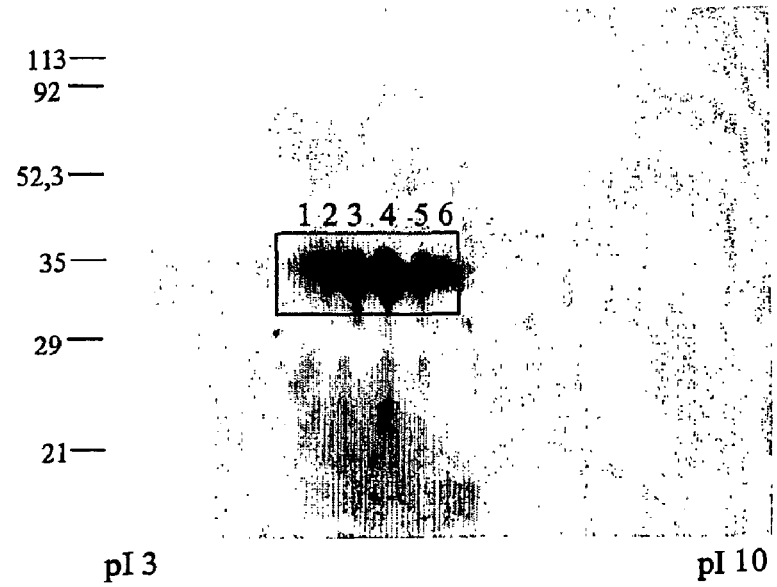
Figure 4:
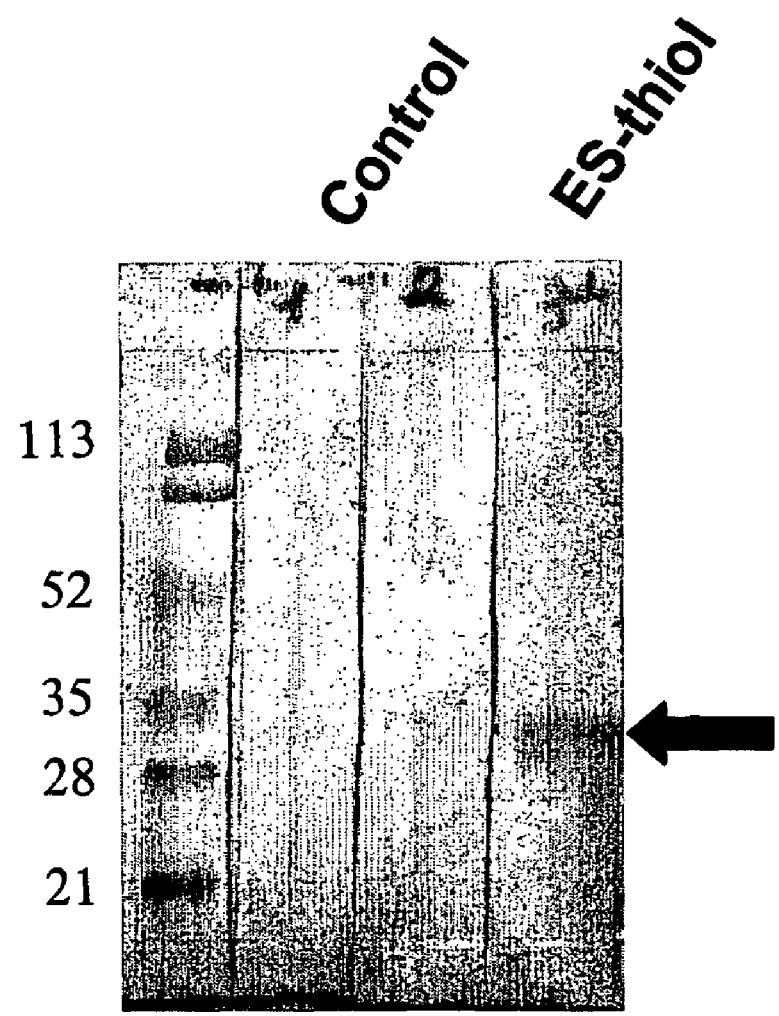

Analysis of the ES-thiol protein fraction on 1D and 2D gel electrophoresis is shown in FIG. 4. ES-thiol comprised a prominent band at ~30 kD as well as 3 lower molecular bands and around 6 peptides in the size range from 45 to 92 kD (FIG. 3A). Analysis of this protein fraction on 2D-gel is shown in FIG. 3B. The prominent 30 kD band visible on the 1D gel migrates in approximately 6 spots between pI 5-7 on 2D-gel. Another 13 fainter spots with pI values ranging from 4 to 8 with molecular masses between 53 and 15 kD were visible in ES-thiol on 2D-gel (FIG. 3B).

Antibody Responses of Immunized Calves

The control animals showed some minor background recognition of a few peptides in ES-thiol (FIG. 4). The ES-thiol group strongly recognized the 30 and the 31 kD antigen (FIG. 4).

Mass-spectrometry Results

The 6 abundant spots at 30 kD were excised from the gel and used in a MALDI-peptide mass fingerprint analysis (boxed in FIG. 3B). Two different proteins were detected in these spots. The peptide mass fingerprint analysis indicated that spots number 3-6 contained the same 31 kD protein, as described above under 4) and spot 1 and 2 contained the 30 kD protein, as described above under 5). The remaining material was used in the LC-MS/MS analysis, which resulted in peptide sequences from spot 1-6. These showed 100% homology with previously characterized excretory-secretory antigen as encoded by the genes encoding a 31 kD and 30 kD *Ostertagia ostertagi* protein, as described in Example 1, under 4) and 5).

Example 3

3.1. Animals

A total of 17 calves, male and female Holstein-cross breed, between 6 and 12 months old from 3 different farms received a natural infection with gastrointestinal nematodes during a first grazing season of at least 6 months.

To confirm the immune status of the calves, reductions in worm burdens were measured after treatment at housing with benzimidazoles and subsequent challenge infection. Calves of farm 1 (n=4) received a natural challenge during one month in the second grazing season (Claerebout et al., *Veterinary Parasitology* 75, 153-167 (1998)). Calves of farm 2 (n=6) and 3 (n=7) received an experimental challenge with 50,000 *O. ostertagi* $L_3$ larvae, one week after treatment. The *O. ostertagi* worm counts of these animals ('immunized' animals) were compared with those from helminth free calves (n=6 for each farm), which received a similar challenge ('primary infected' animals). Reductions in worm counts were 48%, 45% and 24% for calves of farm 1, 2 and 3 respectively.

Sample Collection 3.2. Mucus Collection

Abomasal mucus from all 17 'immunized' animals from the 3 different farms and from the 18 'primary infected' animals was collected by gently scraping the mucosal surface with a glass microscope slide. Mucus scrapings were homogenized with an equal weight of phosphate buffered saline (0.05 M PBS, pH 7.3, 3 mM Na-azide) using an Ultra-turrax homogenizer (13,000 RPM, 3×1 min). The homogenates were centrifuged at 20,000 g for 30 minutes. The supernatant was removed and stored at −70° C. To isolate the immunoglobulins, the supernatant was treated with protein G-agarose beads (Roche). Mucus (1 ml) was centrifuged (14,000 g, 4° C., 30 min) to remove the debris. 200 μl Starting buffer (20 mM $NaH_2PO_4$, pH 7.0) were added to the supernatant to ensure that the pH of the sample stayed neutral. After equilibration of the sample (2 washes with starting buffer) 100 μl Protein G-agarose beads were added. The sample was placed on a rotor for 2 h at 4° C. to allow the binding of the Fc-parts of the Ig's to the beads.

Supernatant was collected and saved together with the first 5 washes (400 μl washing buffer/wash, 20 mM $NaH_2PO_4$, 150 mM NaCl, 2 mM EDTA, pH 7.0). The bound Ig's were eluted with 400 μl elution buffer (100 mM glycine, pH 2.7) until the OD of the elutions was 0. The fractions were immediately neutralized with 20% neutralization buffer (1 M Tris-HCl, pH 9.0). The supernatant/wash fraction was again treated with protein G-agarose beads to ensure that all antibodies present in the mucus sample were collected. The treated mucus samples were pooled in 2 groups for each farm: the 'immunized' group and the 'primary infected' group.

3.3. Antibody Secreting Cell Probes (ASC-probes) Collection

ACS-probes were collected from animals of farm 3 (n=13). Antibody secreting cell probes (ASC-probes) designate the supernatant of a lymph node cell culture that was prepared with the technique originally described by Meeusen and Brandon (*J. Immunol. Methods* 172, 71-76 (1994a); *Eur. J. Immunol.* 24, 469-474 (1994b)). In short, abomasal lymph nodes were collected at necropsy and transported in cold PBS+1% penicillin-streptomycin. Lymphocytes were harvested by cutting and teasing the nodes in 5 ml RPMI medium (Gibco BRL), washed in RPMI medium and centrifuged (1,000 g, 10 min, 4° C.). The red blood cells were lysed by adding 20 ml lysis solution (2% Tris, pH 7.65, 0.8% $NH_4Cl$), for 10 min with gentle shaking. Twenty ml RPMI containing 1% penicillin-streptomycin and 2% horse serum was used to wash the cells 3 times. Cells were resuspended to a final concentration of $5 \times 10^6$ cells/ml in culture medium (RPMI supplemented with 20% horse serum, 1% penicillin-streptomycin, 1% sodium-pyruvate, 1% non-essential amino acids, 1% kanamycin, 0.1% gentamycin and 0.035% β-mercapto-ethanol). Culture flasks containing 50 ml cell suspension were incubated at 37° C. in an atmosphere of 5% $CO_2$ in air without stimulation. After 3 days, the cells were removed by centrifugation (1000 g, 10 min) and 400 ml supernatant per animal were collected. The supernatant (ASC-probes) was concentrated 10 times in a SpeedVac® and pools of antibodies both from the 'immunized' animals and the 'primary infected' animals were made for screening Western Blots and cDNA libraries.

3.4. cDNA Library Screening

*O. ostertagi* $L_3$, 4 and Adult cDNA libraries were constructed in λgt11 phage, propagated on Y1090r⁻ cells and plated by standard methods (Sambrook & Russell, supra). Approximately 100,000 plaques of all 3 libraries were screened with ASC-probes and mucus antibodies. All plaques were first screened with a pool of antibodies of 'immunized' animals from all three farms. All positive plaques were rescreened until a single plaque could be isolated. These positive plaques were rescreened with the antibody pool from 'primary infected' animals from all three farms. The plaques that were exclusively recognized by the antibodies from the 'immune' animals were retained, resuspended in 200 µl of sterile SM buffer (50 mM Tris-HCl, pH 7.5, 100 mM NaCl, 10 mM $MgSO_4$) and stored at 4° C. with a drop of chloroform. The others were designated false positives due to cross recognition of the antibodies from the 'primary infected' animals.

The inserts were amplified by PCR reaction with universal λgt11 primers and the amplicon was gel-purified with a gel purification kit (Qiagen). The cDNA fragment was subcloned into pGEM-T vector (Promega) and transformed into DH5α *E. coli* cells. Following blue-white screening (IPTG/X-gal) and PCR with SP6 and T7 vector primers, recombinant clones were selected and plasmid DNA was isolated using the Qiagen plasmid isolation kit. The nucleotide sequence of the cDNA clones was determined by the dideoxy chain terminator method using fluorescent Big-Dye™ terminators in a 377 automated DNA sequencer (PE Biosystems). Assembly and analysis of nucleotide and deduced amino acid sequences were performed using the DNASTAR® software program.

Results of Example 3:

The screening method using local antibodies obtained from mucus and Antibody Secreting Cell (ASC) culture supernatant made it possible that two additional novel genes encoding vaccine components were found:

1) a gene of 900 nucleotides was found in both the larval $L_4$ stage and in the Adult stage cDNA library. The nucleotide sequence of this gene is given in SEQ ID NO: 11. The gene encodes a protein with a length of 300 amino acids and a molecular weight of about 24 kD. The protein has an isoelectric point of pI 6.6. The amino acid sequence of the protein is given in SEQ ID NO: 12.

Figure 5:
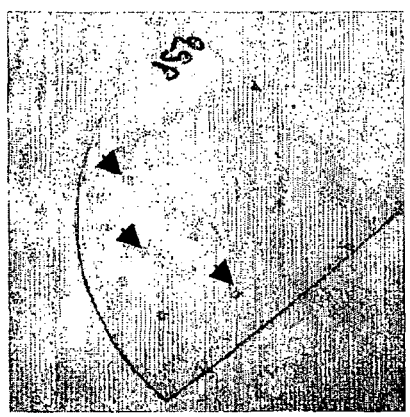
Figure 5:
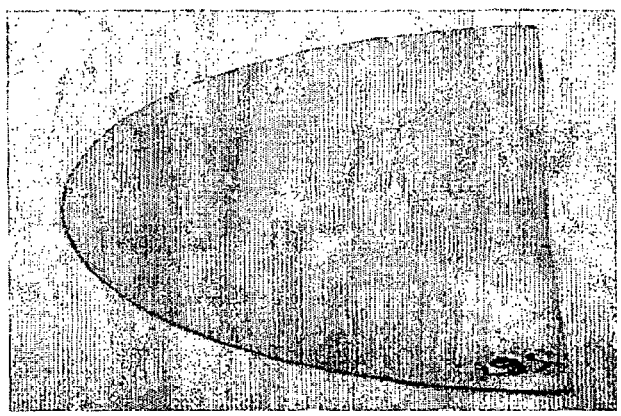

The arrows in FIG. 5, left picture, show how bacteria expressing this protein are specifically recognized by antibodies found in the supernatant of lymph nodes isolated from immune animals. The importance of this finding is underlined by the fact that antibodies isolated from primary infected animals do not at all react with these clones. This clearly indicates the importance of this protein in the induction of immunity. Further characterization of this protein is outlined in Example 4.

2) a gene of 1238 nucleotides was found in the larval $L_3$ stage and in the Adult stage cDNA library. The nucleotide sequence of this gene is given in SEQ ID NO: 13. The gene encodes a protein of 65 kD. The amino acid sequence of the protein is given in SEQ ID NO: 14. The arrows in FIG. 6, left picture, show how bacteria expressing this protein are specifically recognized by antibodies isolated from the mucus of immune animals. Again, the importance of this finding is underlined by the fact that antibodies isolated from primary infected animals do not at all react with these clones. This clearly indicates the importance of this protein in the induction of immunity.

Details on the identification of the full-length gene are outlined in Example 5.

Example 4

4.1 Cloning of the Gene for the 24 kD Protein

A 653 bp fragment was amplified from the gene clone encoding the 24 kD protein (De Maere et al., *Parasitoloy*, 125, 383-391 (2002)) by PCR using primers that also incorporate restriction endonuclease sites (underlined). Primers used were:

```
24kForw
5'-GAATTCATGAAGTTGGTCGTG-3'      (SEQ ID NO:19)
and

24kRev
5'-CTCGAGTCAATAGATCCTTGTG-3'.   (SEQ ID NO:20)
```

The PCR product was digested with restriction enzymes EcoRI and XhoI, gel-purified (Qiagen kit) and cloned in frame into the T7-/6× Hisitidine-tagged vector pET21a (Novagen). The correct reading frame was confirmed by sequencing and the construct was transformed into the BL21 (DE3) strain of *Escherichia coli*. Recombinant protein expression was induced by addition of isopropyl-β thio galactosidase during 2 h at 37° C.

Cells were centrifuged, resuspended in PBS and lysed by adding 0,1 volume of lysozyme. After a cycle of freezing (−70° C.) and thawing, cell debris was spun down and supernatant was collected. Cell debris was resuspended in the T7-BindBuffer® (+6M Ureum) for 1 h on ice to resuspend the insoluble proteins.

Recombinant proteins were purified over a T7-tag affinity column and afterwards by a His-bind resin column.

4.2 Polyclonal Antibodies

100 µg of recombinant protein was injected 3 times intramuscularly with 3 weeks interval in a rabbit. Pre-immune blood was taken just before the first immunization and the final bleeding was done 3 weeks after the last immunization.

4.3 Sample Collection

Mucus collection and Antibody Secreting Cell Probe collection are described in example 3 above (sections 3.3 and 3.4), and in De Maere et al. (2002, supra).

4.4 Western Blotting

Recognition of native or recombinant 24 kD protein by ASC probes, Mucus antibodies or rabbit anti-24 kD protein serum was evaluated by Western blotting. Ten µg of *Ostertagia* extract or Excretion-Secretion product was fractionated using 10% SDS-PAGE under reducing conditions and then transferred onto a PVDF membrane. The blot sections were cut into strips, blocked for 2 h in 10% normal horse serum in PBST, and probed overnight with ASC probes. Mucus antibodies or rabbit anti-24 kD protein serum and conjugate were then added: Rabbit anti-bovine-HPRO (H+L) (Jackson Imunoresearch Laboratories Inc.) at 1:8000, or HRPO-conjugated goat anti-rabbit (Sigma) at 1:6000 in 2% normal horse serum in PBST. Strips were incubated for one hour. Recognized antigens were visualized by adding 0.05% 3,3 diaminobenzidine tetrachloride in PBS containing 0.01% $H_2O_2$ (v/v).

4.5 Quantitative RT PCR

RT-PCR was used to investigate transcripts of the gene encoding the 24 kD protein in *O. ostertagi* parasitic life stages. Three microgram of total RNA from each life stage ($L_3$, $L_3$-exsheathed, $L_4$ and Adult) was used for the cDNA synthesis using an oligo(dT) primer (Superscript®, Life technologies). The oligonucleotide primers used for detection of transcripts of the gene encoding the 24 kD protein were designed to amplify an approximately 300 basepair long cDNA. Actin (Oo-act), described by Vercauteren et al. (*Molecular and Biochemical Parasitology*, 126, 201-208 (2003)), was used as a constitutively expressed 'housekeeping' gene control to determine the uniformity of the reverse transcription reactions.

cDNA of the gene encoding the 24 kD protein was amplified and quantified using the Light Cycler® and the lightcycler-faststart DNA master SYBR green I kit (Roche, Mannheim, Germany). The reaction mixture consist of a master mix containing Taq DNA polymerase, dNTP mixture and SYBR green I, 2 mM $MgCl_2$, 5 pM of each primer and 2 µl of template cDNA in total of 20 µl. Confirmation of the specificity of the PCR-products was performed by subjecting these products to a melting curve analysis, subsequent agarose gel electrophoresis and sequencing. The PCR analysis was performed in triplicate and quantification occurred using external standards of 24 kD protein and Oo-act cDNA. Calculation was performed with the Lightcycler analysis software. The relative amount of 24 kD protein expression was plotted as a ratio ((copy number of 24 kD protein/copy number of house keeping gene)×10).

Results of Example 4:

Recombinant 24 kD protein (FIG. 7A) was recognized by ASC-probes and Mucus antibodies from immune animals (FIG. 7B-C). This indicates that the epitopes of the recombinant protein resemble those of the native protein and that the recombinant protein has the same protective capacities as the native protein. Antibodies raised against the recombinant protein in rabbits, therefore also recognize the native protein on 1D gel (FIG. 7D) and 2D gel (FIG. 8A)

Antibodies to recombinant 24 kD protein were used to specify the stage specific expression of the protein on Western Blot (FIG. 8B).

RT-PCR showed expression of the protein in all life stages, especially in the $L_3$ with sheath and in the $L_4$ stage (FIG. 9A).

As the 24 kD protein is expressed predominantly in $L_3$ and 4 stage larvae, a vaccine based on this protein interferes with the development of the $L_3$ (the infective stage) and the $L_4$ larval parasite stages. Thereby reducing or preventing the establishment of an *Ostertagia* infection. This in turn leads to a reduced worm-load in the animal with all beneficial consequences set out herein.

Example 5

Obtaining the Full Length Gene Encoding the 65 kD Protein

Utilizing the Ad clone (De Maere et al., *Parasitoloy*, 125, 383-391 (2002)) as the basis for specific primer design, the complete sequence of the gene as depicted in SEQ ID NO: 13 was obtained by the technique of 5'/3'-Rapid Amplification of cDNA Ends (RACE). The 5'-RACE kit from GibcoBRL was employed to identify the 5' end of the gene for the 65 kD protein. First strand cDNA was produced in a reverse transcription reaction using the specific primer 65Rev1 (see below) on 2 µg Adult RNA. This cDNA was poly C tailed at its 3' end with terminal deoxytransferase and used as a template in a PCR with the Abridged Anchor Primer (AAP, GibcoBRL):

```
                                          (SEQ ID NO:21)
AAP: 5'-GGCCACGCGTCGACTAGTACGGGIIGGGIIGGGIIG-3'
``` and gene specific primer 65Rev2 (see below). The 5' RACE PCR product was cloned and sequenced.

The 3'-RACE kit from GibcoBRL was employed to identify the 3' end of the gene for the 65 kD protein. Briefly, first strand cDNA was produced in a reverse transcription reaction using an oligo(dT)-containing Adapter Primer (AP) on 2 µg Adult RNA. This cDNA was used as a template in a PCR with a gene specific primer 65 kForw (see below) and the Universal Amplification Primer (UAP, GibcoBRL):

```
                                          (SEQ ID NO: 22)
UAP  5'-CUACUACUACUAGGCCACGCGTCGACTAGTAC-3'
```

The 3' RACE PCR product was cloned and sequenced.

Alignment of all the sequence data made it possible to design new gene specific primers comprising the start- and stopcodon, For65 and Rev65 (see below). The SUPERSCRIPT™ Preamplification System for First Strand cDNA Synthesis (GibcoBRL) was used to create template for a PCR with these primers to obtain the full length cDNA.

Gene specific primers employed to identify the full length coding sequence of the cDNA for the 65 kD protein are:

```
65Rev1:
5'-CAGCAATGGATACCGAATGAC-3'              (SEQ ID NO: 23)

65Rev2:
5'-AGTGACTTCATCATTGCTGGTG-3'             (SEQ ID NO: 24)

65kForw:
5'-TGATGATGAAGAACGAGAGGA-3'              (SEQ ID NO: 25)

For65:
5'-GGATCCATGAGGCTGATATTGCTCATTTTA-3'     (SEQ ID NO: 26)

Rev65:
5'-CTCGAGGCAGAGTCCACACGACTTTGG-3'        (SEQ ID NO: 27)
```

Quantitative RT-PCR

RT-PCR was used to investigate transcripts of the gene for the 65 kD protein in the parasitic *O. ostertagi* life stages. Three microgram of total RNA from each life stage ($L_3$, $L_3$-exsheathed, $L_4$ and Adult) were used for the cDNA synthesis using an oligo(dT) primer (Superscript, Life technologies). The oligonucleotide primers used for detection of the transcript for the 65 kD protein were designed to amplify an approximately 300-500 basepair long cDNA. Actin (Oo-act), described by Vercauteren et al. (2003, supra), was used as a constitutively expressed 'housekeeping' gene control to determine the uniformity of the reverse transcription reactions.

cDNA for the 65 kD protein was amplified and quantified as described in Example 4, section 4.5.

Results of Example 5:

The complete coding sequence of the gene encoding the 65 kD protein, as depicted SEQ ID NO:13 is 1722 bp long and codes for a protein with a molecular weight of 65 kD (SEQ ID NO:14). The N-terminal aa sequence contains a putative signal-sequence that is probably cleaved between aa 16 and 17 (Glycine-Glycine). The encoded protein sequence contains 5 N-glycosylation sites, a zinc-binding region (cd00203: HEXXHALGFXHEXXRXDR) and a pfam01400 domain (HEXXHXXG) this places it in the family of Astacin's (Peptidase family M12A).

RT-PCR revealed stage specific expression of the gene for the 65 kD protein by *Ostertagia ostertagi*. Transcripts were detected in the $L_3$ and the Adult stages with particular higher expression level in the Adult life stage (FIG. 9B). This is in conformity with the screening of the cDNA library (De Maere et al., 2002, supra).

As the 65 kD protein is expressed predominantly in Adult stages, a vaccine based on this protein interferes with Adult parasite development. This leads to reduced production of eggs, which in turn reduces the contamination of the fields. This reduces the worm-burden and contamination levels later in the season.

Example 6

Expression in the Baculovirus Expression Vector System

The coding regions for the 65, 28, 31, and 24 kD proteins of the invention were subcloned from their respective vectors into a pFastBac® plasmid (Invitrogen) using standard techniques. These FastBac constructs were transfected into Sf9 insect cells, to produce recombinant baculoviruses, according to the manufacturer's instructions (Invitrogen). Next expression cultures were run, using Sf9 and Sf158 insect cells, which were cultured in microcarrier spinner flasks of 100 and 250 ml. Serum free culture media used were CCM3™ (Hyclone), and SF900-II™ (Invitrogen). Cells were infected at an m.o.i. of 0.1-0.5 and cultured for 34 days. Then cultures were centrifuged, culture supernatant was harvested, and cell pellets were resuspended 10× concentrated in PBS. TRITONX-100® non-ionic polyethylene glycol octylphenyl ether detergent was added to all samples to a concentration of 0.2% v/v. Samples were extracted overnight at room temperature, centrifuged, and supernatants were stored at −20° C. until use.

Extract-supernatants were run on standard SDS/PAGE gels alongside appropriate markers, blotted onto Immobilon-P® transfer membrane (Millipore), membranes were stained with anti His-tag monoclonal antibody (Sigma), and visualized.

Figure 10:
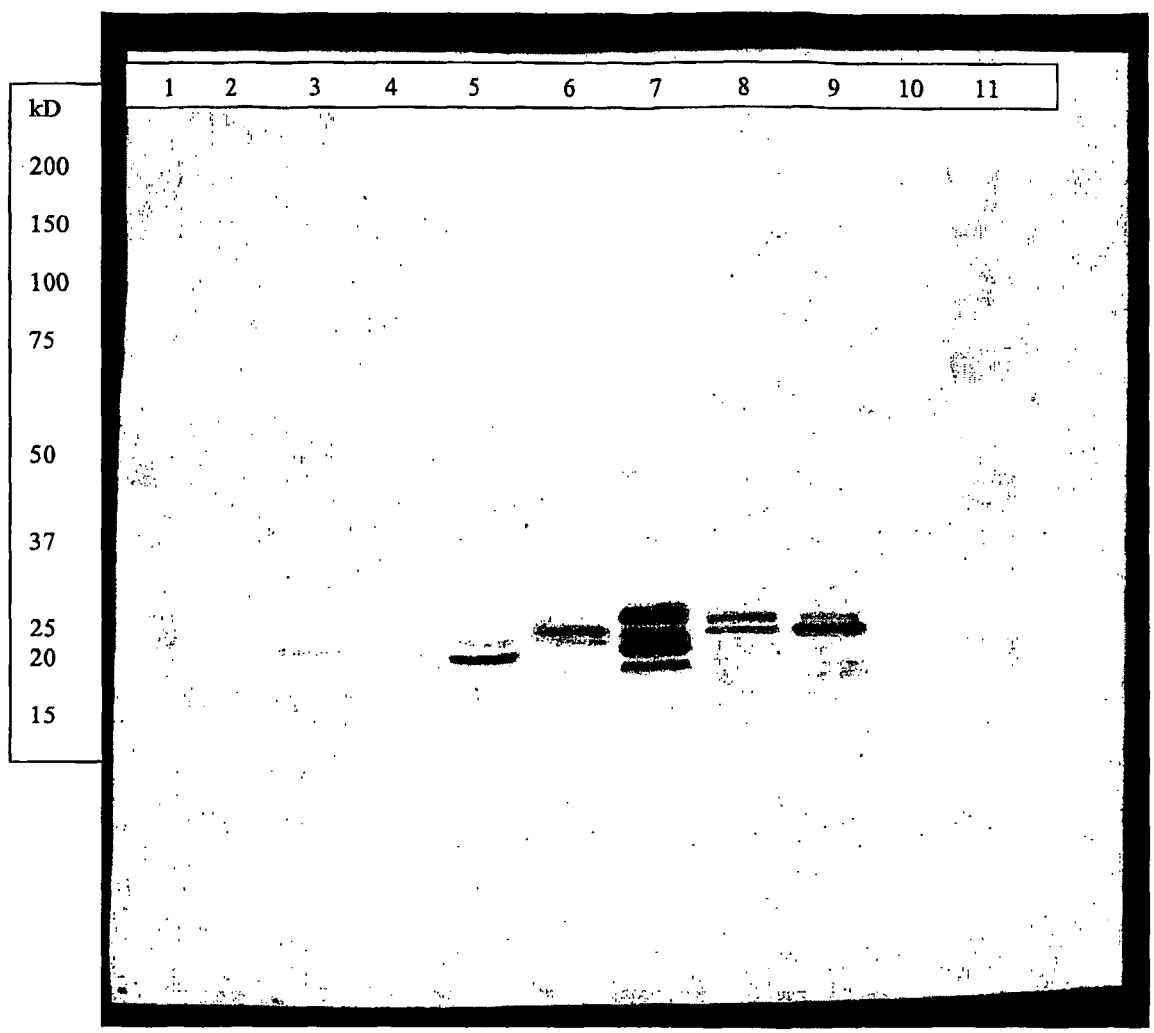

FIG. 10 shows the results of these baculovirus expressions in Western blot; the proteins of the invention were most abundant in the insect cell-pellet samples. These have been used to formulate vaccines for vaccinations.

Legend to the Figures

FIG. 1: Dot-blot of lysed bacteria comprising a nucleotide sequence encoding (at least an immunogenic part of) the protein as depicted in SEQ ID NO: 8. Screening was done with specifically prepared anti-excretory-secretory rabbit antiserum (See Example 1). An arrow indicates one of the positive clones.

Figure 2:
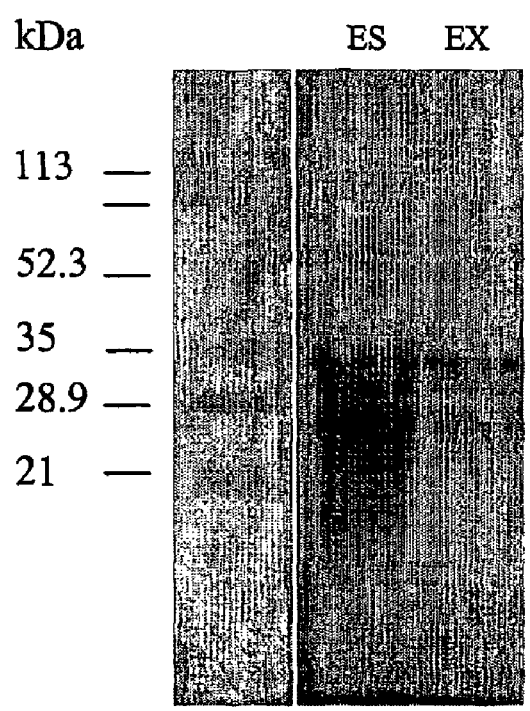
Figure 2:
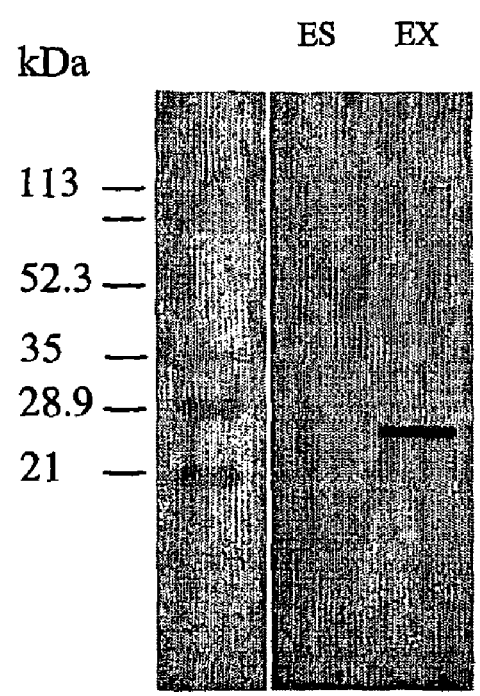

FIG. 2: Western-blots; in panel 2B of the 28 kD protein with anti-ES and anti-EX rabbit antiserum (see Example 1), and in panel 2C of the 25 kD protein with anti-ES and anti-EX rabbit antiserum (see Example 1).

FIG. 3: Analysis of the ES-thiol protein fraction (see also Example 2); in panel 3A a 1D gel electrophoresis, and in panel 3B a 2D gel electrophoresis. The 2D gel shows the 31 kD protein (the four right-most spots in the boxed area) and the 30 kD protein (the two left-most spots in the boxed area).

FIG. 4: Antibody response of ES-thiol-immunized calves against ES-fraction proteins.

FIG. 5: Dot-blot of lysed bacteria comprising a nucleotide sequence encoding the 24 kD protein as depicted in SEQ ID NO: 12. Screening was done with specifically prepared antibodies from lymph node supernatant of immune animals (left-hand picture). (See also Examples 3, and 4). Arrows indicate some of the positive clones. The right-hand picture shows a comparable dot-blot, now incubated with antibodies of primary infected animals. With these antibodies no positive clones are recognized.

Figure 6:
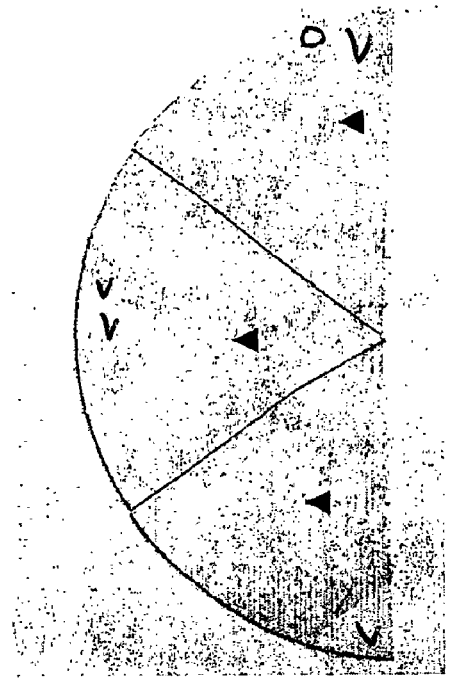
Figure 6:
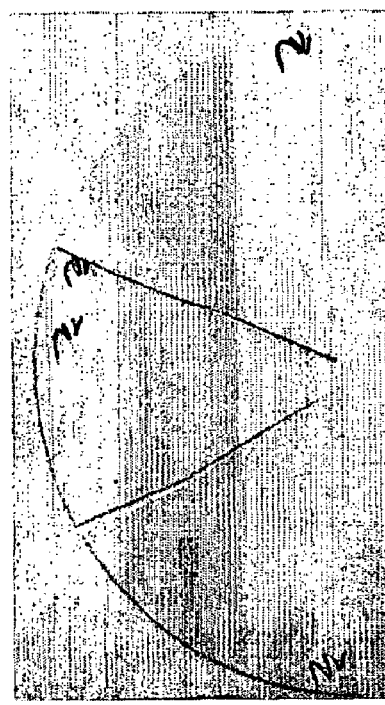

FIG. 6: Dot-blot of lysed bacteria comprising a nucleotide sequence encoding the 65 kD protein as depicted in SEQ ID NO: 14. Screening was done with specifically prepared antibodies from mucus of immune animals (left-hand picture). (See also Examples 3, and 5). Arrows indicate some of the positive clones. The right-hand picture shows a comparable dot-blot, now incubated with antibodies of primary infected animals. With these antibodies no positive clones are recognized.

Figure 7:
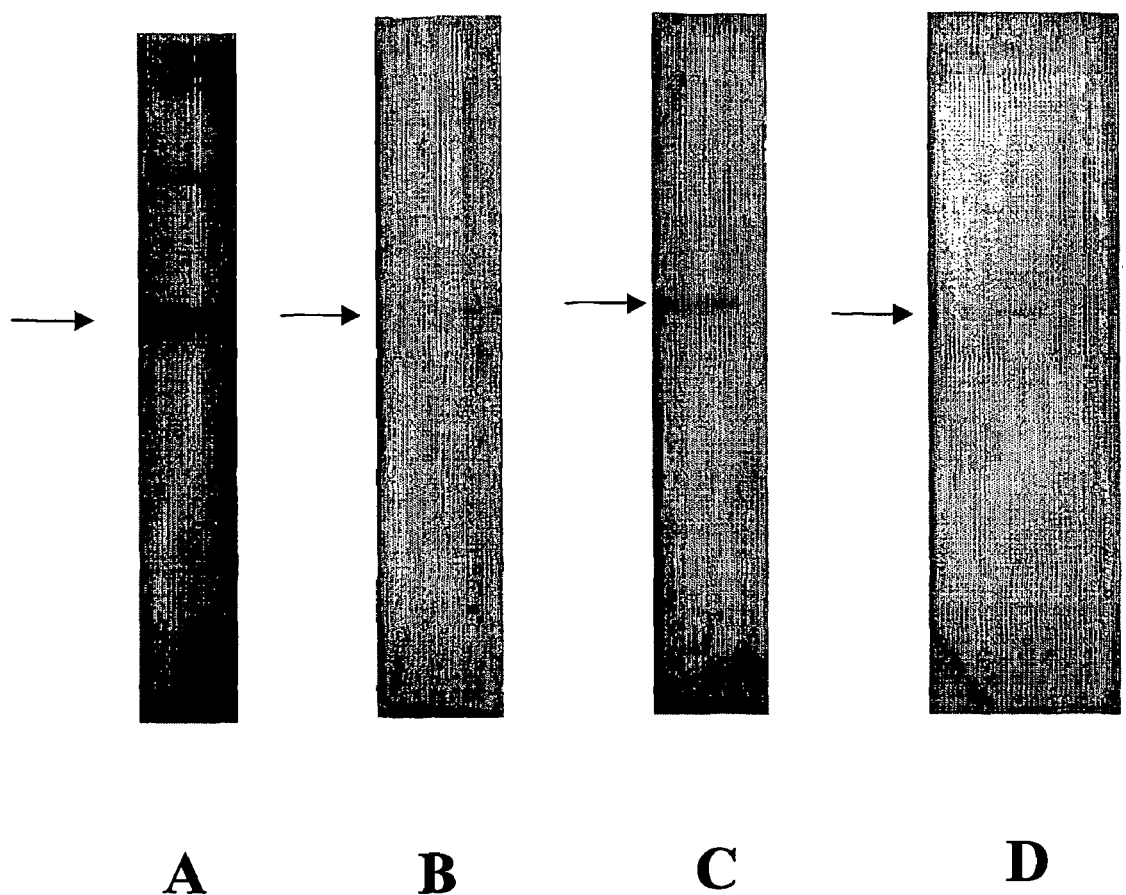

FIG. 7: Electrophoretic characterization of the 24 kD protein; in panel 7A: result of expression of recombinant 24 kD protein in *E. coli*; panel 7B: a Western blot of rec 24 kD protein developed with ASC probe antibodies from immune animals; in panel 7C: Western blot of rec 24 kD protein developed with Mucus antibodies from immune animals, and panel 7D: Western Blot of $L_4$ extract developed with rabbit anti-24 kD protein antibodies.

Figure 8:
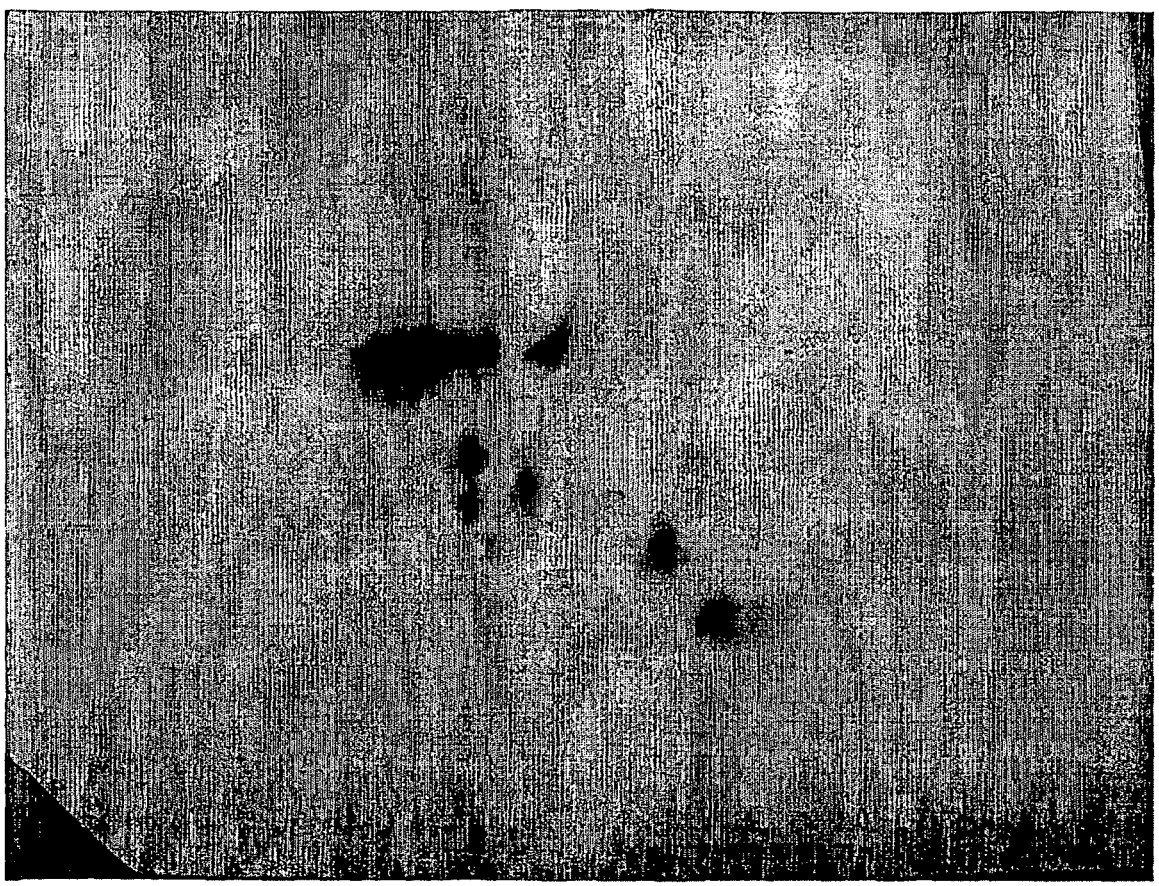
Figure 8:
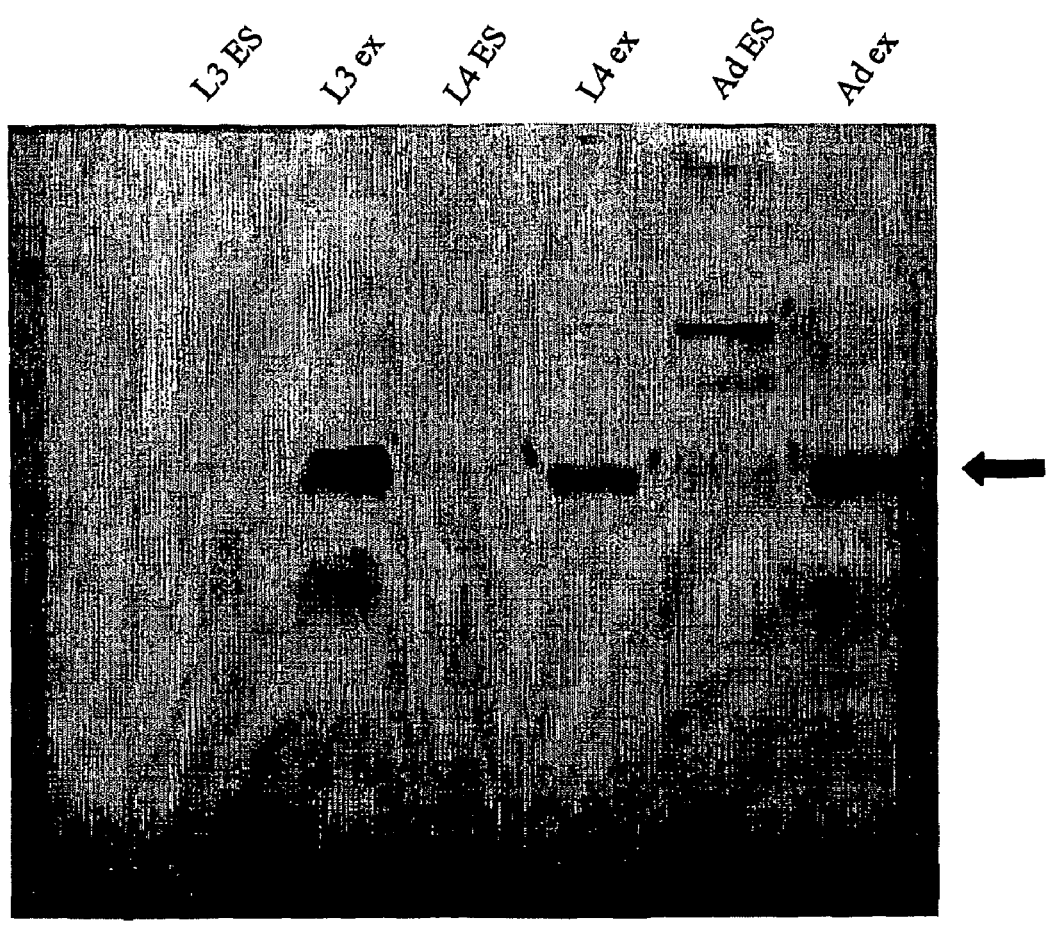

FIG. 8: Characterization of the 24 kD protein; in panel 8A: 2D gel electrophoresis and Western Blotting of Adult extract from *Ostertagia ostertagi*, developed with specific antibodies against *E. coli* expressed recombinant 24 kD protein, raised in rabbits, and panel 8B: stage specific expression of 24 kD protein, developed with anti-rec 24 kD protein antibodies.

Figure 9:
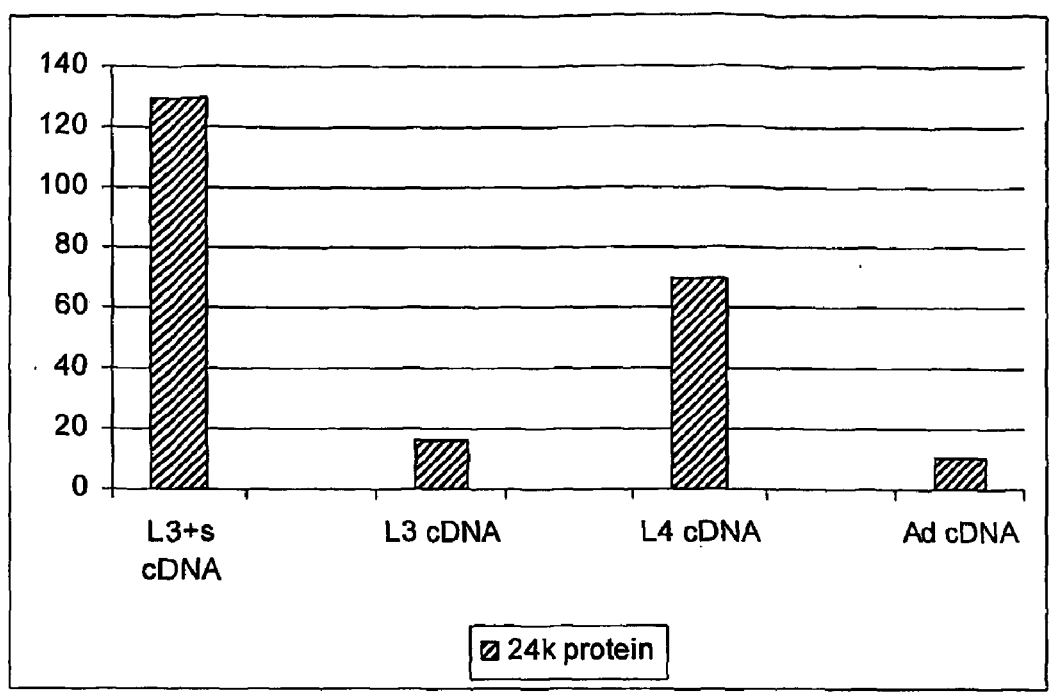
Figure 9:
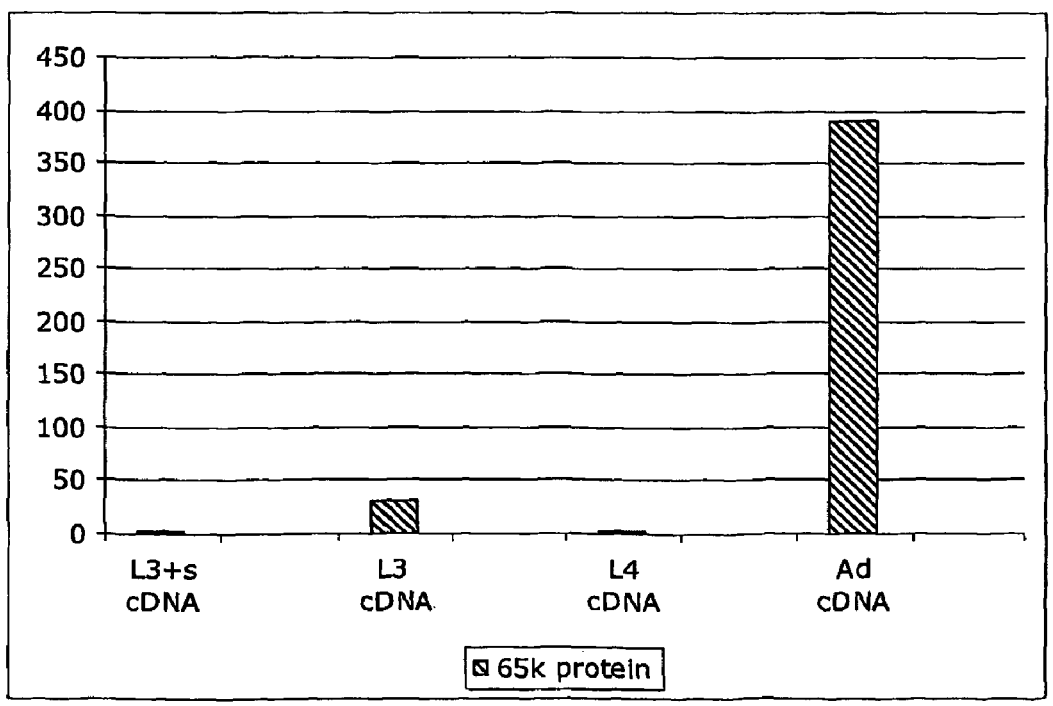

FIG. 9: Results of quantitative RT-PCRs to detect stage specific expression; in panel 9A for 24 kD protein (see Example 4), and in panel 9B for the 65 kD protein (see Example 5).

FIG. 10: Western blot of *Ostertagia* proteins expressed in the baculovirus expression vector system (see Example 6), staining was with anti-His antibody Lanes 1 and 11: BioRad Protein Precision Marker®

Lane 2: 65 kD protein, supernatant+0.2% TX-100

Lane 3: 65 kD protein, cell-pellet in PBS+0.2% TX-100 (5× conc.)

Lane 4: 28 kD protein, supernatant+0.2% TX-100

Lane 5: 28 kD protein, cell-pellet in PBS+0.2% TX-100 (5× conc.)

Lane 6: 31 kD protein, supernatant+0.2% TX-100

Lane 7: 31 kD protein, cell-pellet in PBS+0.2% TX-100 (5× conc.)

Lane 8: 24 kD protein, supernatant+0.2% TX-100

Lane 9: 24 kD protein, cell-pellet in PBS+0.2% TX-100 (5× conc.)

Lane 10: empty

The invention claimed is:

1. An isolated and purified 30 kD *Ostertagia ostertagi* protein, wherein said protein has the sequence of SEQ ID NO:10.

2. An isolated and purified *Ostertagia ostertagi* protein, wherein said protein is encoded by a nucleic acid with the sequence of SEQ ID NO:9.

3. A diagnostic kit comprising the protein according to claim 1.

* * * * *

SEQUENCE LISTING

<160> NUMBER OF SEQ ID NOS: 27

<210> SEQ ID NO 1
<211> LENGTH: 828
<212> TYPE: DNA
<213> ORGANISM: Ostertagia ostertagi
<220> FEATURE:
<221> NAME/KEY: CDS
<222> LOCATION: (11)..(721)

<400> SEQUENCE: 1

```
gcagctcggt atg cag gca cta atc ggt att gct gcc cta tac ctg gtg         49
           Met Gln Ala Leu Ile Gly Ile Ala Ala Leu Tyr Leu Val
               1               5                  10 ctg gtg aca tca aat acc gaa gca ggt ttt tgc tgc cca gca gat cta         97
Leu Val Thr Ser Asn Thr Glu Ala Gly Phe Cys Cys Pro Ala Asp Leu
    15                  20                  25 aac caa act gat gag gca aga maa atc ttc ctc gat ttt cac aat caa        145
Asn Gln Thr Asp Glu Ala Arg Xaa Ile Phe Leu Asp Phe His Asn Gln
30                  35                  40                  45 gtt cgc cgt gat ata gca ggt gca agc ccg ttg ctc aac ctc acc gga        193
Val Arg Arg Asp Ile Ala Gly Ala Ser Pro Leu Leu Asn Leu Thr Gly
                50                  55                  60 gct gtt car atg cga aat gtt ctc ggt cca gct aag aac atg tac aga        241
Ala Val Gln Met Arg Asn Val Leu Gly Pro Ala Lys Asn Met Tyr Arg
            65                  70                  75 atg gac tgg gac tgc aat ctg gaa gca aaa gca aag gca atg att tgg        289
Met Asp Trp Asp Cys Asn Leu Glu Ala Lys Ala Lys Ala Met Ile Trp
        80                  85                  90 cca tgc act acg cct ctg cca ata gac acg agt att cca caa aat ctc        337
Pro Cys Thr Thr Pro Leu Pro Ile Asp Thr Ser Ile Pro Gln Asn Leu
    95                  100                 105 gct car tgg cta ctt ttc caa aac agt cag gaa amt gaa gtg ttg acg        385
Ala Gln Trp Leu Leu Phe Gln Asn Ser Gln Glu Xaa Glu Val Leu Thr
110                 115                 120                 125 caa acg ccc tgg tct tgg gta acc gca tca cta cga aat ctt caa cct        433
Gln Thr Pro Trp Ser Trp Val Thr Ala Ser Leu Arg Asn Leu Gln Pro
                130                 135                 140 gat aca gaa gct aac att tat aac tgg caa att aga cca cta tcc aac        481
Asp Thr Glu Ala Asn Ile Tyr Asn Trp Gln Ile Arg Pro Leu Ser Asn
            145                 150                 155 att gcg aac tgg caa aac cta aaa gtt gga tgt gct cac aaa gtg tgc        529
Ile Ala Asn Trp Gln Asn Leu Lys Val Gly Cys Ala His Lys Val Cys
        160                 165                 170 aaa ttc ccc acc ggg aca aat atg gtt gtg tct tgc gct tat ggc ggc        577
Lys Phe Pro Thr Gly Thr Asn Met Val Val Ser Cys Ala Tyr Gly Gly
    175                 180                 185 gaa gta ctc caa gat aac gaa gtt gta tgg gac aag gga cca act tgc        625
Glu Val Leu Gln Asp Asn Glu Val Val Trp Asp Lys Gly Pro Thr Cys
190                 195                 200                 205 atg tgc aat gct tat ccc aac tcg ttc tgc tgc aac aat ctg tgt gac        673
Met Cys Asn Ala Tyr Pro Asn Ser Phe Cys Cys Asn Asn Leu Cys Asp
                210                 215                 220 aca ata gct gct gcg aca ctt cgc aag cag cct tgt aaa tcg act tga        721
Thr Ile Ala Ala Ala Thr Leu Arg Lys Gln Pro Cys Lys Ser Thr
            225                 230                 235 agcgaaaagg cgttggtgat gtcccgaaga gaacggaagt gatcacatca cagtatccca        781
taatgtcgtt catcataata aacgcacttc tctgaaaaaa aaaaaaa                      828
```

```
<210> SEQ ID NO 2
<211> LENGTH: 236
<212> TYPE: PRT
<213> ORGANISM: Ostertagia ostertagi
<220> FEATURE:
<221> NAME/KEY: misc_feature
<222> LOCATION: (37)..(37)
<223> OTHER INFORMATION: The xaa at location 37 stands for Lys, or Gln.
<220> FEATURE:
<221> NAME/KEY: misc_feature
<222> LOCATION: (121)..(121)
<223> OTHER INFORMATION: The xaa at location 121 stands for Asn, or Thr.

<400> SEQUENCE: 2

Met Gln Ala Leu Ile Gly Ile Ala Ala Leu Tyr Leu Val Leu Val Thr
1               5                   10                  15

Ser Asn Thr Glu Ala Gly Phe Cys Cys Pro Ala Asp Leu Asn Gln Thr
            20                  25                  30

Asp Glu Ala Arg Xaa Ile Phe Leu Asp Phe His Asn Gln Val Arg Arg
        35                  40                  45

Asp Ile Ala Gly Ala Ser Pro Leu Leu Asn Leu Thr Gly Ala Val Gln
50                  55                  60

Met Arg Asn Val Leu Gly Pro Ala Lys Asn Met Tyr Arg Met Asp Trp
65                  70                  75                  80

Asp Cys Asn Leu Glu Ala Lys Ala Lys Ala Met Ile Trp Pro Cys Thr
                85                  90                  95

Thr Pro Leu Pro Ile Asp Thr Ser Ile Pro Gln Asn Leu Ala Gln Trp
            100                 105                 110

Leu Leu Phe Gln Asn Ser Gln Glu Xaa Glu Val Leu Thr Gln Thr Pro
        115                 120                 125

Trp Ser Trp Val Thr Ala Ser Leu Arg Asn Leu Gln Pro Asp Thr Glu
130                 135                 140

Ala Asn Ile Tyr Asn Trp Gln Ile Arg Pro Leu Ser Asn Ile Ala Asn
145                 150                 155                 160

Trp Gln Asn Leu Lys Val Gly Cys Ala His Lys Val Cys Lys Phe Pro
                165                 170                 175

Thr Gly Thr Asn Met Val Val Ser Cys Ala Tyr Gly Gly Glu Val Leu
            180                 185                 190

Gln Asp Asn Glu Val Val Trp Asp Lys Gly Pro Thr Cys Met Cys Asn
        195                 200                 205

Ala Tyr Pro Asn Ser Phe Cys Cys Asn Asn Leu Cys Asp Thr Ile Ala
210                 215                 220

Ala Ala Thr Leu Arg Lys Gln Pro Cys Lys Ser Thr
225                 230                 235

<210> SEQ ID NO 3
<211> LENGTH: 306
<212> TYPE: DNA
<213> ORGANISM: Ostertagia ostertagi
<220> FEATURE:
<221> NAME/KEY: CDS
<222> LOCATION: (3)..(284)
<220> FEATURE:
<221> NAME/KEY: misc_feature
<222> LOCATION: (10)..(10)
<223> OTHER INFORMATION: n is a, c, g, or t
<220> FEATURE:
<221> NAME/KEY: misc_feature
<222> LOCATION: (16)..(16)
<223> OTHER INFORMATION: n is a, c, g, or t
<220> FEATURE:
<221> NAME/KEY: misc_feature
```

```
<222> LOCATION: (82)..(82)
<223> OTHER INFORMATION: n is a, c, g, or t
<220> FEATURE:
<221> NAME/KEY: misc_feature
<222> LOCATION: (226)..(226)
<223> OTHER INFORMATION: n is a, c, g, or t
<220> FEATURE:
<221> NAME/KEY: misc_feature
<222> LOCATION: (240)..(240)
<223> OTHER INFORMATION: n is a, c, g, or t
<220> FEATURE:
<221> NAME/KEY: misc_feature
<222> LOCATION: (248)..(248)
<223> OTHER INFORMATION: n is a, c, g, or t

<400> SEQUENCE: 3 gc ggc cgc gnc gac cnt gtg atc agc atc atg gct ctg tgg ccc gtg         47
   Gly Arg Xaa Asp Xaa Val Ile Ser Ile Met Ala Leu Trp Pro Val
   1               5                  10                  15 gac cgt ttc gag cgc atg ctg gaa gag ccg ttc ang cgt gtg gat cgt         95
Asp Arg Phe Glu Arg Met Leu Glu Glu Pro Phe Xaa Arg Val Asp Arg
                20                  25                  30 ttc tgc ccg atg aga gat gcg gac tgg atg agc cgt cag att atg ccc        143
Phe Cys Pro Met Arg Asp Ala Asp Trp Met Ser Arg Gln Ile Met Pro
            35                  40                  45 tac tgg aga gat gcc gat cac tct gtg ctt cat gtg gga aat caa aca        191
Tyr Trp Arg Asp Ala Asp His Ser Val Leu His Val Gly Asn Gln Thr
        50                  55                  60 aag gat gtc gtg aat gac gag aag aaa ttc gca gnc gct ttg gat gtg        239
Lys Asp Val Val Asn Asp Glu Lys Lys Phe Ala Xaa Ala Leu Asp Val
    65                  70                  75 nca cac ttn agg cca gaa gag ttg aag gta caa ttg gaa gtg acg            284
Xaa His Xaa Arg Pro Glu Glu Leu Lys Val Gln Leu Glu Val Thr
80                  85                  90 tgaccttaca atcgaaggac at                                               306

<210> SEQ ID NO 4
<211> LENGTH: 94
<212> TYPE: PRT
<213> ORGANISM: Ostertagia ostertagi
<220> FEATURE:
<221> NAME/KEY: misc_feature
<222> LOCATION: (3)..(3)
<223> OTHER INFORMATION: The xaa at location 3 stands for Asp, Gly, Ala,
      or Val.
<220> FEATURE:
<221> NAME/KEY: misc_feature
<222> LOCATION: (5)..(5)
<223> OTHER INFORMATION: The xaa at location 5 stands for His, Arg, Pro,
      or Leu.
<220> FEATURE:
<221> NAME/KEY: misc_feature
<222> LOCATION: (27)..(27)
<223> OTHER INFORMATION: The xaa at location 27 stands for Lys, Arg,
      Thr, or Met.
<220> FEATURE:
<221> NAME/KEY: misc_feature
<222> LOCATION: (75)..(75)
<223> OTHER INFORMATION: The xaa at location 75 stands for Asp, Gly,
      Ala, or Val.
<220> FEATURE:
<221> NAME/KEY: misc_feature
<222> LOCATION: (80)..(80)
<223> OTHER INFORMATION: The xaa at location 80 stands for Thr, Ala,
      Pro, or Ser.
<220> FEATURE:
<221> NAME/KEY: misc_feature
<222> LOCATION: (82)..(82)
<223> OTHER INFORMATION: The xaa at location 82 stands for Leu, or Phe.

<400> SEQUENCE: 4
```

```
Gly Arg Xaa Asp Xaa Val Ile Ser Ile Met Ala Leu Trp Pro Val Asp
1               5                   10                  15

Arg Phe Glu Arg Met Leu Glu Glu Pro Phe Xaa Arg Val Asp Arg Phe
            20                  25                  30

Cys Pro Met Arg Asp Ala Asp Trp Met Ser Arg Gln Ile Met Pro Tyr
            35                  40                  45

Trp Arg Asp Ala Asp His Ser Val Leu His Val Gly Asn Gln Thr Lys
        50                  55                  60

Asp Val Val Asn Asp Glu Lys Lys Phe Ala Xaa Ala Leu Asp Val Xaa
65                  70                  75                  80

His Xaa Arg Pro Glu Glu Leu Lys Val Gln Leu Glu Val Thr
                85                  90
```

<210> SEQ ID NO 5
<211> LENGTH: 583
<212> TYPE: DNA
<213> ORGANISM: Ostertagia ostertagi
<220> FEATURE:
<221> NAME/KEY: CDS
<222> LOCATION: (2)..(583)

<400> SEQUENCE: 5

```
g gct ttt atc gga aaa ccc gca ccc gac ttc gcc aca aag gcc gtc tat      49
  Ala Phe Ile Gly Lys Pro Ala Pro Asp Phe Ala Thr Lys Ala Val Tyr
  1               5                   10                  15 aat ggc gac ttc atc gac gtg aaa ctg tct gac tac aag ggc aag tac        97
Asn Gly Asp Phe Ile Asp Val Lys Leu Ser Asp Tyr Lys Gly Lys Tyr
            20                  25                  30 acc gtc ctc ttc ttc tat cca ctg gat ttc acg ttt gtc tgt cct acg       145
Thr Val Leu Phe Phe Tyr Pro Leu Asp Phe Thr Phe Val Cys Pro Thr
        35                  40                  45 gaa atc atc gcc ttt tcc gac cgt gtc gaa gaa ttc aaa aaa atc gat       193
Glu Ile Ile Ala Phe Ser Asp Arg Val Glu Glu Phe Lys Lys Ile Asp
    50                  55                  60 gct gcg gtc ctc gct tgt tca amt gat tcc gtt ttc tct cat ctg gcg       241
Ala Ala Val Leu Ala Cys Ser Xaa Asp Ser Val Phe Ser His Leu Ala
65                  70                  75                  80 tgg atc aat act cct cgc aag atg ggc ggc ctt ggt gac atg aac att       289
Trp Ile Asn Thr Pro Arg Lys Met Gly Gly Leu Gly Asp Met Asn Ile
                85                  90                  95 ccc gtt ctt gct gac acc aac cac caa att gca aag gac tat ggt gta       337
Pro Val Leu Ala Asp Thr Asn His Gln Ile Ala Lys Asp Tyr Gly Val
            100                 105                 110 ctg aaa gaa gac gaa gga atc gct tac aga ggt ctt ttc att att gac       385
Leu Lys Glu Asp Glu Gly Ile Ala Tyr Arg Gly Leu Phe Ile Ile Asp
        115                 120                 125 cct aag gga att ctg cga cag atc act gtc aat gac ctt cct gtc ggt       433
Pro Lys Gly Ile Leu Arg Gln Ile Thr Val Asn Asp Leu Pro Val Gly
    130                 135                 140 cgc tct gtg gat gag act ctc cgt ctg gtg cag gcc ttc caa tac gtt       481
Arg Ser Val Asp Glu Thr Leu Arg Leu Val Gln Ala Phe Gln Tyr Val
145                 150                 155                 160 gac aag cat ggt gag gtg tgc cca gct ggt tgg act cct gga aaa gct       529
Asp Lys His Gly Glu Val Cys Pro Ala Gly Trp Thr Pro Gly Lys Ala
                165                 170                 175 acc atc aag cca ggt gtc aag gac agc aag gag tac ttc agc aaa gca       577
Thr Ile Lys Pro Gly Val Lys Asp Ser Lys Glu Tyr Phe Ser Lys Ala
            180                 185                 190 aac taa                                                                583
```

Asn

<210> SEQ ID NO 6
<211> LENGTH: 193
<212> TYPE: PRT
<213> ORGANISM: Ostertagia ostertagi
<220> FEATURE:
<221> NAME/KEY: misc_feature
<222> LOCATION: (72)..(72)
<223> OTHER INFORMATION: The xaa at location 72 stands for Asn, or Thr.

<400> SEQUENCE: 6

```
Ala Phe Ile Gly Lys Pro Ala Pro Asp Phe Ala Thr Lys Ala Val Tyr
1               5                   10                  15

Asn Gly Asp Phe Ile Asp Val Lys Leu Ser Asp Tyr Lys Gly Lys Tyr
            20                  25                  30

Thr Val Leu Phe Phe Tyr Pro Leu Asp Phe Thr Phe Val Cys Pro Thr
        35                  40                  45

Glu Ile Ile Ala Phe Ser Asp Arg Val Glu Phe Lys Lys Ile Asp
    50                  55                  60

Ala Ala Val Leu Ala Cys Ser Xaa Asp Ser Val Phe Ser His Leu Ala
65                  70                  75                  80

Trp Ile Asn Thr Pro Arg Lys Met Gly Gly Leu Gly Asp Met Asn Ile
                85                  90                  95

Pro Val Leu Ala Asp Thr Asn His Gln Ile Ala Lys Asp Tyr Gly Val
            100                 105                 110

Leu Lys Glu Asp Glu Gly Ile Ala Tyr Arg Gly Leu Phe Ile Ile Asp
        115                 120                 125

Pro Lys Gly Ile Leu Arg Gln Ile Thr Val Asn Asp Leu Pro Val Gly
    130                 135                 140

Arg Ser Val Asp Glu Thr Leu Arg Leu Val Gln Ala Phe Gln Tyr Val
145                 150                 155                 160

Asp Lys His Gly Glu Val Cys Pro Ala Gly Trp Thr Pro Gly Lys Ala
                165                 170                 175

Thr Ile Lys Pro Gly Val Lys Asp Ser Lys Glu Tyr Phe Ser Lys Ala
            180                 185                 190
```

Asn

<210> SEQ ID NO 7
<211> LENGTH: 693
<212> TYPE: DNA
<213> ORGANISM: Ostertagia ostertagi
<220> FEATURE:
<221> NAME/KEY: CDS
<222> LOCATION: (1)..(693)
<220> FEATURE:
<221> NAME/KEY: misc_feature
<222> LOCATION: (11)..(11)
<223> OTHER INFORMATION: n is a, c, g, or t
<220> FEATURE:
<221> NAME/KEY: misc_feature
<222> LOCATION: (35)..(36)
<223> OTHER INFORMATION: n is a, c, g, or t
<220> FEATURE:
<221> NAME/KEY: misc_feature
<222> LOCATION: (41)..(41)
<223> OTHER INFORMATION: n is a, c, g, or t
<220> FEATURE:
<221> NAME/KEY: misc_feature
<222> LOCATION: (43)..(43)
<223> OTHER INFORMATION: n is a, c, g, or t
<220> FEATURE:
<221> NAME/KEY: misc_feature
<222> LOCATION: (53)..(53)

<223> OTHER INFORMATION: n is a, c, g, or t
<220> FEATURE:
<221> NAME/KEY: misc_feature
<222> LOCATION: (67)..(67)
<223> OTHER INFORMATION: n is a, c, g, or t
<220> FEATURE:
<221> NAME/KEY: misc_feature
<222> LOCATION: (199)..(199)
<223> OTHER INFORMATION: n is a, c, g, or t
<220> FEATURE:
<221> NAME/KEY: misc_feature
<222> LOCATION: (555)..(555)
<223> OTHER INFORMATION: n is a, c, g, or t
<220> FEATURE:
<221> NAME/KEY: misc_feature
<222> LOCATION: (590)..(590)
<223> OTHER INFORMATION: n is a, c, g, or t
<220> FEATURE:
<221> NAME/KEY: misc_feature
<222> LOCATION: (648)..(648)
<223> OTHER INFORMATION: n is a, c, g, or t
<220> FEATURE:
<221> NAME/KEY: misc_feature
<222> LOCATION: (662)..(662)
<223> OTHER INFORMATION: n is a, c, g, or t
<220> FEATURE:
<221> NAME/KEY: misc_feature
<222> LOCATION: (669)..(669)
<223> OTHER INFORMATION: n is a, c, g, or t
<220> FEATURE:
<221> NAME/KEY: misc_feature
<222> LOCATION: (682)..(682)
<223> OTHER INFORMATION: n is a, c, g, or t

<400> SEQUENCE: 7

```
cta act cct tng cat cca acg cgt tgg gag ctc tnn cta tng ngg gaa      48
Leu Thr Pro Xaa His Pro Thr Arg Trp Glu Leu Xaa Leu Xaa Xaa Glu
1               5                   10                  15 ttg cna tgt ggt ggc gac nac tcc tgg agc ccg tca gta tcg gcg gaa      96
Leu Xaa Cys Gly Gly Asp Xaa Ser Trp Ser Pro Ser Val Ser Ala Glu
            20                  25                  30 ttc gcg gcc gcg tcg acc gtg ggt gtg gcc ctc gcg gtc cac caa aca     144
Phe Ala Ala Ala Ser Thr Val Gly Val Ala Leu Ala Val His Gln Thr
        35                  40                  45 ctt gac ctg ctt cct ctg aag cca cgc aag gag tac gtc ttc cgc ttt     192
Leu Asp Leu Leu Pro Leu Lys Pro Arg Lys Glu Tyr Val Phe Arg Phe
    50                  55                  60 gaa gga nat gtt cac tcc gga atc ccg ctc cca acc gac acc acc atc     240
Glu Gly Xaa Val His Ser Gly Ile Pro Leu Pro Thr Asp Thr Thr Ile
65                  70                  75                  80 tct cgc ata cag gct atg gta cat gtc cag atc cct gac gac cac cac     288
Ser Arg Ile Gln Ala Met Val His Val Gln Ile Pro Asp Asp His His
                85                  90                  95 gcc att ctc aag ctg aga gat gtt cgc ttt gct act gga gaa gac gaa     336
Ala Ile Leu Lys Leu Arg Asp Val Arg Phe Ala Thr Gly Glu Asp Glu
            100                 105                 110 cgc aga gaa ctc ttc aaa ccg atc gat gac ctg aaa atg cgc aca atc     384
Arg Arg Glu Leu Phe Lys Pro Ile Asp Asp Leu Lys Met Arg Thr Ile
        115                 120                 125 tca agg gag cac ctc gat ctc ctt gag ttg cca gtc cgt ttt gtc tac     432
Ser Arg Glu His Leu Asp Leu Leu Glu Leu Pro Val Arg Phe Val Tyr
    130                 135                 140 aag aac ggc atg att tcc gat gta atc ttt gtc gac aag gag gag acc     480
Lys Asn Gly Met Ile Ser Asp Val Ile Phe Val Asp Lys Glu Glu Thr
145                 150                 155                 160 tgg tcc cgc cag cgt gaa gcc gat ctg tca tca aca tgc tcc act tta     528
Trp Ser Arg Gln Arg Glu Ala Asp Leu Ser Ser Thr Cys Ser Thr Leu
                165                 170                 175
```

-continued

```
acc tcc aca aga tgg gac gaa ctg acn agc ttt aca atg gac agg tcc      576
Thr Ser Thr Arg Trp Asp Glu Leu Thr Ser Phe Thr Met Asp Arg Ser
        180                 185                 190 aag gtg gac ccg tng aca aac gag tac ttt cac tgg tta ccc gaa ccg      624
Lys Val Asp Pro Xaa Thr Asn Glu Tyr Phe His Trp Leu Pro Glu Pro
            195                 200                 205 aac cca ttc gaa ggg aaa ctt gtn aag gtt ggc tta cnc cgg ttn tta      672
Asn Pro Phe Glu Gly Lys Leu Val Lys Val Gly Leu Xaa Arg Xaa Leu
        210                 215                 220 aag aaa aaa ngg acc ttt tgg                                          693
Lys Lys Lys Xaa Thr Phe Trp
225                 230
```

<210> SEQ ID NO 8
<211> LENGTH: 231
<212> TYPE: PRT
<213> ORGANISM: Ostertagia ostertagi
<220> FEATURE:
<221> NAME/KEY: misc_feature
<222> LOCATION: (4)..(4)
<223> OTHER INFORMATION: The xaa at location 4 stands for Trp, Ser, or
      Leu.
<220> FEATURE:
<221> NAME/KEY: misc_feature
<222> LOCATION: (12)..(12)
<223> OTHER INFORMATION: The xaa at location 12 stands for Tyr, Trp,
      Cys, Ser, Leu, or Phe.
<220> FEATURE:
<221> NAME/KEY: misc_feature
<222> LOCATION: (14)..(14)
<223> OTHER INFORMATION: The xaa at location 14 stands for Trp, Ser, or
      Leu.
<220> FEATURE:
<221> NAME/KEY: misc_feature
<222> LOCATION: (15)..(15)
<223> OTHER INFORMATION: The xaa at location 15 stands for Arg, Gly,
      or Trp.
<220> FEATURE:
<221> NAME/KEY: misc_feature
<222> LOCATION: (18)..(18)
<223> OTHER INFORMATION: The xaa at location 18 stands for Gln, Arg,
      Pro, or Leu.
<220> FEATURE:
<221> NAME/KEY: misc_feature
<222> LOCATION: (23)..(23)
<223> OTHER INFORMATION: The xaa at location 23 stands for Asn, Asp,
      His, or Tyr.
<220> FEATURE:
<221> NAME/KEY: misc_feature
<222> LOCATION: (67)..(67)
<223> OTHER INFORMATION: The xaa at location 67 stands for Asn, Asp,
      His, or Tyr.
<220> FEATURE:
<221> NAME/KEY: misc_feature
<222> LOCATION: (197)..(197)
<223> OTHER INFORMATION: The xaa at location 197 stands for Trp, Ser,
      or Leu.
<220> FEATURE:
<221> NAME/KEY: misc_feature
<222> LOCATION: (221)..(221)
<223> OTHER INFORMATION: The xaa at location 221 stands for His, Arg,
      Pro, or Leu.
<220> FEATURE:
<221> NAME/KEY: misc_feature
<222> LOCATION: (223)..(223)
<223> OTHER INFORMATION: The xaa at location 223 stands for Leu, or Phe.
<220> FEATURE:
<221> NAME/KEY: misc_feature
<222> LOCATION: (228)..(228)
<223> OTHER INFORMATION: The xaa at location 228 stands for Arg, Gly, or
      Trp.

<400> SEQUENCE: 8

```
Leu Thr Pro Xaa His Pro Thr Arg Trp Glu Leu Xaa Leu Xaa Xaa Glu
1               5                   10                  15

Leu Xaa Cys Gly Gly Asp Xaa Ser Trp Ser Pro Ser Val Ser Ala Glu
        20                  25                  30

Phe Ala Ala Ser Thr Val Gly Val Ala Leu Ala Val His Gln Thr
        35                  40                  45

Leu Asp Leu Leu Pro Leu Lys Pro Arg Lys Glu Tyr Val Phe Arg Phe
50                  55                  60

Glu Gly Xaa Val His Ser Gly Ile Pro Leu Pro Thr Asp Thr Thr Ile
65                  70                  75                  80

Ser Arg Ile Gln Ala Met Val His Val Gln Ile Pro Asp Asp His His
                85                  90                  95

Ala Ile Leu Lys Leu Arg Asp Val Arg Phe Ala Thr Gly Glu Asp Glu
            100                 105                 110

Arg Arg Glu Leu Phe Lys Pro Ile Asp Asp Leu Lys Met Arg Thr Ile
        115                 120                 125

Ser Arg Glu His Leu Asp Leu Leu Glu Leu Pro Val Arg Phe Val Tyr
    130                 135                 140

Lys Asn Gly Met Ile Ser Asp Val Ile Phe Val Asp Lys Glu Glu Thr
145                 150                 155                 160

Trp Ser Arg Gln Arg Glu Ala Asp Leu Ser Ser Thr Cys Ser Thr Leu
                165                 170                 175

Thr Ser Thr Arg Trp Asp Glu Leu Thr Ser Phe Thr Met Asp Arg Ser
            180                 185                 190

Lys Val Asp Pro Xaa Thr Asn Glu Tyr Phe His Trp Leu Pro Glu Pro
        195                 200                 205

Asn Pro Phe Glu Gly Lys Leu Val Lys Val Gly Leu Xaa Arg Xaa Leu
    210                 215                 220

Lys Lys Lys Xaa Thr Phe Trp
225             230

<210> SEQ ID NO 9
<211> LENGTH: 763
<212> TYPE: DNA
<213> ORGANISM: Ostertagia ostertagi
<220> FEATURE:
<221> NAME/KEY: CDS
<222> LOCATION: (11)..(706)

<400> SEQUENCE: 9
gagaactgct atg tcg gcg gct gtt gta gtt gct gtt ctc ctg gcc ctg          49
           Met Ser Ala Ala Val Val Val Ala Val Leu Leu Ala Leu
           1               5                   10 ttc tcc tat gcc gaa gca ggc ttt tgt tgt ccg aat agt cta agc caa        97
Phe Ser Tyr Ala Glu Ala Gly Phe Cys Cys Pro Asn Ser Leu Ser Gln
    15                  20                  25 agt gac agc gcg agg cag att ttc ctc gat ttt cac aat gat gtt cgt       145
Ser Asp Ser Ala Arg Gln Ile Phe Leu Asp Phe His Asn Asp Val Arg
30                  35                  40                  45 cga aat ata gca ctt gga aat ggt ttg ata aac tgg aca gta aat gca       193
Arg Asn Ile Ala Leu Gly Asn Gly Leu Ile Asn Trp Thr Val Asn Ala
                50                  55                  60 gac gcg gtc att ctt ggt cca gct cag aac atg tac aaa gtg gac tgg       241
Asp Ala Val Ile Leu Gly Pro Ala Gln Asn Met Tyr Lys Val Asp Trp
            65                  70                  75 gat tgc aac ttg gaa gaa gta gca gca caa cag att gcg cca tgc aat       289
Asp Cys Asn Leu Glu Glu Val Ala Ala Gln Gln Ile Ala Pro Cys Asn
        80                  85                  90
```

```
gat ccc cta ccg ata aat acc agc ctg gct caa aat atc gct aga tgg    337
Asp Pro Leu Pro Ile Asn Thr Ser Leu Ala Gln Asn Ile Ala Arg Trp
 95             100                 105 ctg tac ttc aaa gac agt gaa gaa gag aca gtt ctg caa caa gta tcg    385
Leu Tyr Phe Lys Asp Ser Glu Glu Glu Thr Val Leu Gln Gln Val Ser
110             115                 120                 125 tgg tat tgg gtg agc gca tcg ctg gga ttt atg aaa ggc acg aaa ctt    433
Trp Tyr Trp Val Ser Ala Ser Leu Gly Phe Met Lys Gly Thr Lys Leu
                130                 135                 140 gac caa ttt gct aac cag tgg gct gaa cct cta gca aac att gca aac    481
Asp Gln Phe Ala Asn Gln Trp Ala Glu Pro Leu Ala Asn Ile Ala Asn
145                 150                 155 tat aga aac cga aag gtt gga tgt gcc cat aag atc tgc ccc gct cag    529
Tyr Arg Asn Arg Lys Val Gly Cys Ala His Lys Ile Cys Pro Ala Gln
        160                 165                 170 caa aac atg gta gta tcc tgc gtg tat gga agc ccc aaa ctt gca ccg    577
Gln Asn Met Val Val Ser Cys Val Tyr Gly Ser Pro Lys Leu Ala Pro
            175                 180                 185 aac gaa gtt atc tgg cag gaa gga aag gct tgt gtg tgc gac gct cgt    625
Asn Glu Val Ile Trp Gln Glu Gly Lys Ala Cys Val Cys Asp Ala Arg
190                 195                 200                 205 cca gat tca ttc tgc tgc gac aac ctg tgt gac acg cga gat gct gcg    673
Pro Asp Ser Phe Cys Cys Asp Asn Leu Cys Asp Thr Arg Asp Ala Ala
                210                 215                 220 agt gtt cgc cac cag tgt tgc gcg tcg cca tga agcgaaaaga aattggtagt  726
Ser Val Arg His Gln Cys Cys Ala Ser Pro
                225                 230 caccccgaat aaatattca tgcaaaaaaa aaaaaaa                            763

<210> SEQ ID NO 10
<211> LENGTH: 231
<212> TYPE: PRT
<213> ORGANISM: Ostertagia ostertagi

<400> SEQUENCE: 10

Met Ser Ala Ala Val Val Ala Val Leu Leu Ala Leu Phe Ser Tyr
 1               5                   10                  15

Ala Glu Ala Gly Phe Cys Cys Pro Asn Ser Leu Ser Gln Ser Asp Ser
                20                  25                  30

Ala Arg Gln Ile Phe Leu Asp Phe His Asn Asp Val Arg Arg Asn Ile
            35                  40                  45

Ala Leu Gly Asn Gly Leu Ile Asn Trp Thr Val Asn Ala Asp Ala Val
        50                  55                  60

Ile Leu Gly Pro Ala Gln Asn Met Tyr Lys Val Asp Trp Asp Cys Asn
65                  70                  75                  80

Leu Glu Glu Val Ala Ala Gln Gln Ile Ala Pro Cys Asn Asp Pro Leu
                85                  90                  95

Pro Ile Asn Thr Ser Leu Ala Gln Asn Ile Ala Arg Trp Leu Tyr Phe
                100                 105                 110

Lys Asp Ser Glu Glu Glu Thr Val Leu Gln Gln Val Ser Trp Tyr Trp
            115                 120                 125

Val Ser Ala Ser Leu Gly Phe Met Lys Gly Thr Lys Leu Asp Gln Phe
        130                 135                 140

Ala Asn Gln Trp Ala Glu Pro Leu Ala Asn Ile Ala Asn Tyr Arg Asn
145                 150                 155                 160

Arg Lys Val Gly Cys Ala His Lys Ile Cys Pro Ala Gln Gln Asn Met
                165                 170                 175
```

```
Val Val Ser Cys Val Tyr Gly Ser Pro Lys Leu Ala Pro Asn Glu Val
            180                 185                 190

Ile Trp Gln Glu Gly Lys Ala Cys Val Cys Asp Ala Arg Pro Asp Ser
        195                 200                 205

Phe Cys Cys Asp Asn Leu Cys Asp Thr Arg Asp Ala Ala Ser Val Arg
    210                 215                 220

His Gln Cys Cys Ala Ser Pro
225                 230

<210> SEQ ID NO 11
<211> LENGTH: 893
<212> TYPE: DNA
<213> ORGANISM: Ostertagia ostertagi
<220> FEATURE:
<221> NAME/KEY: CDS
<222> LOCATION: (1)..(684)
<220> FEATURE:
<221> NAME/KEY: misc_feature
<222> LOCATION: (813)..(813)
<223> OTHER INFORMATION: n is a, c, g, or t
<220> FEATURE:
<221> NAME/KEY: misc_feature
<222> LOCATION: (858)..(858)
<223> OTHER INFORMATION: n is a, c, g, or t

<400> SEQUENCE: 11 atg aag ttg gtc gtg ctc tgc gtt ctg tgt gga atc gct ctt gct gcc      48
Met Lys Leu Val Val Leu Cys Val Leu Cys Gly Ile Ala Leu Ala Ala
1               5                   10                  15 ccg aga cag aaa cgc ctt act gtg ggc acg atc gct gtc acc gga gga      96
Pro Arg Gln Lys Arg Leu Thr Val Gly Thr Ile Ala Val Thr Gly Gly
            20                  25                  30 gtc ggc gga tcc acg ggg tgt gta gtg act gga aat gtc ctc tac gca     144
Val Gly Gly Ser Thr Gly Cys Val Val Thr Gly Asn Val Leu Tyr Ala
        35                  40                  45 aac ggt ttc cgc ctt cgt gaa ctc aac cca tcg gag cag caa gaa ctc     192
Asn Gly Phe Arg Leu Arg Glu Leu Asn Pro Ser Glu Gln Gln Glu Leu
    50                  55                  60 gta aac tat gag aag cag gtg gcc gac tac aaa gcg gct gtg aag caa     240
Val Asn Tyr Glu Lys Gln Val Ala Asp Tyr Lys Ala Ala Val Lys Gln
65                  70                  75                  80 gcc ctc aag gaa cgc cag gaa agc ctg aaa tcg cgc atg gct ggt aag     288
Ala Leu Lys Glu Arg Gln Glu Ser Leu Lys Ser Arg Met Ala Gly Lys
                85                  90                  95 aag gag aag gct gtg act ccc aag gag gaa gat cta ccc aaa gct cca     336
Lys Glu Lys Ala Val Thr Pro Lys Glu Glu Asp Leu Pro Lys Ala Pro
            100                 105                 110 cag aag ccc tca ttc tgc act gag gac gac acc acc cag ttc tac ttt     384
Gln Lys Pro Ser Phe Cys Thr Glu Asp Asp Thr Thr Gln Phe Tyr Phe
        115                 120                 125 gat gga tgc atg gtt cag ggc aac aag gtc tac gtt ggc aac aca ttc     432
Asp Gly Cys Met Val Gln Gly Asn Lys Val Tyr Val Gly Asn Thr Phe
    130                 135                 140 gcg cgc gat ttg gac cag aac gag att caa gag ctg aag gag ttt gag     480
Ala Arg Asp Leu Asp Gln Asn Glu Ile Gln Glu Leu Lys Glu Phe Glu
145                 150                 155                 160 aag aag cag act gtc tac cag gaa tac gtc cag aag cag att caa gcg     528
Lys Lys Gln Thr Val Tyr Gln Glu Tyr Val Gln Lys Gln Ile Gln Ala
                165                 170                 175 caa gtg agc aat ctg ttc ggc ggt gcc gac ttc ttt tca tcg ttc ttc     576
Gln Val Ser Asn Leu Phe Gly Gly Ala Asp Phe Phe Ser Ser Phe Phe
            180                 185                 190
```

```
aac ggc gga tct gag aaa ggc tct tca acc acc act gtg gcc cca gtg    624
Asn Gly Gly Ser Glu Lys Gly Ser Ser Thr Thr Thr Val Ala Pro Val
            195                 200                 205 ctt cct gaa gat gca cca gaa caa cca gct ggg ccc aac ttt tgc aca    672
Leu Pro Glu Asp Ala Pro Glu Gln Pro Ala Gly Pro Asn Phe Cys Thr
    210                 215                 220 agg atc tat tga tgggtatttt ttatgatgac aaagtattta aataaatgca        724
Arg Ile Tyr
225 gtagttgcct gttgctgtga attccacagc actcctactc acggtgtcga ctggtgattt  784 agtcacttta tttgcaatat tttttatgng ttaccgcaat tcgttgtata tttgtgttat  844 aaacattaac atcnaaaaaa aaaaaaaaaa aaaaaaaaaa aaaaaaaaa              893

<210> SEQ ID NO 12
<211> LENGTH: 227
<212> TYPE: PRT
<213> ORGANISM: Ostertagia ostertagi

<400> SEQUENCE: 12

Met Lys Leu Val Val Leu Cys Val Leu Cys Gly Ile Ala Leu Ala Ala
1               5                   10                  15

Pro Arg Gln Lys Arg Leu Thr Val Gly Thr Ile Ala Val Thr Gly Gly
            20                  25                  30

Val Gly Gly Ser Thr Gly Cys Val Val Thr Gly Asn Val Leu Tyr Ala
        35                  40                  45

Asn Gly Phe Arg Leu Arg Glu Leu Asn Pro Ser Glu Gln Gln Glu Leu
    50                  55                  60

Val Asn Tyr Glu Lys Gln Val Ala Asp Tyr Lys Ala Ala Val Lys Gln
65                  70                  75                  80

Ala Leu Lys Glu Arg Gln Glu Ser Leu Lys Ser Arg Met Ala Gly Lys
                85                  90                  95

Lys Glu Lys Ala Val Thr Pro Lys Glu Glu Asp Leu Pro Lys Ala Pro
            100                 105                 110

Gln Lys Pro Ser Phe Cys Thr Glu Asp Thr Thr Gln Phe Tyr Phe
        115                 120                 125

Asp Gly Cys Met Val Gln Gly Asn Lys Val Tyr Val Gly Asn Thr Phe
    130                 135                 140

Ala Arg Asp Leu Asp Gln Asn Glu Ile Gln Glu Leu Lys Glu Phe Glu
145                 150                 155                 160

Lys Lys Gln Thr Val Tyr Gln Glu Tyr Val Gln Lys Gln Ile Gln Ala
                165                 170                 175

Gln Val Ser Asn Leu Phe Gly Gly Ala Asp Phe Phe Ser Ser Phe Phe
            180                 185                 190

Asn Gly Gly Ser Glu Lys Gly Ser Ser Thr Thr Thr Val Ala Pro Val
        195                 200                 205

Leu Pro Glu Asp Ala Pro Glu Gln Pro Ala Gly Pro Asn Phe Cys Thr
    210                 215                 220

Arg Ile Tyr
225

<210> SEQ ID NO 13
<211> LENGTH: 1761
<212> TYPE: DNA
<213> ORGANISM: Ostertagia ostertagi
<220> FEATURE:
<221> NAME/KEY: CDS
```

<222> LOCATION: (1)..(1725)

<400> SEQUENCE: 13

```
atg agg ctg ata ttg ctc att tta ctc ttg gtt gtt gcc act aat ggg       48
Met Arg Leu Ile Leu Leu Ile Leu Leu Val Val Ala Thr Asn Gly
1               5                   10                  15 ggc ata att gac aaa ctg aaa gga ttg ttc act gga gaa ggc ggc ttt       96
Gly Ile Ile Asp Lys Leu Lys Gly Leu Phe Thr Gly Glu Gly Gly Phe
            20                  25                  30 gga caa aaa gtg aag aat gca act gct gtt ggc ttc aaa aag ctc ttc      144
Gly Gln Lys Val Lys Asn Ala Thr Ala Val Gly Phe Lys Lys Leu Phe
        35                  40                  45 gaa aac acg gca ctc ttc aga atc aat gat aag atc agg agc atg aag      192
Glu Asn Thr Ala Leu Phe Arg Ile Asn Asp Lys Ile Arg Ser Met Lys
    50                  55                  60 gaa aaa gtg ttg aag acc ttg gaa cta tca cca gca atg atg aag tca      240
Glu Lys Val Leu Lys Thr Leu Glu Leu Ser Pro Ala Met Met Lys Ser
65                  70                  75                  80 ctg caa kmg agg cta rwg aaw tsg cgr cck yct rma grw cga yma wrt      288
Leu Gln Xaa Arg Leu Xaa Xaa Xaa Arg Xaa Xaa Xaa Xaa Arg Xaa Xaa
                85                  90                  95 rsr mga gmt sss aga crc gtw kka ygc rag gtc art aaa aat agt gag

-continued

| | | | | | | | | | | | | | |
|---|---|---|---|---|---|---|---|---|---|---|---|---|---|
| gca | tcg | tac | aat | aat | aag | cca | aca | atg | gtg | ccg | ttt | gat | gtg gac tat | 960 |
| Ala | Ser | Tyr | Asn | Asn | Lys | Pro | Thr | Met | Val | Pro | Phe | Asp | Val Asp Tyr |
| 305 | | | | 310 | | | | | 315 | | | | 320 |

```
gca tcg tac aat aat aag cca aca atg gtg ccg ttt gat gtg gac tat      960
Ala Ser Tyr Asn Asn Lys Pro Thr Met Val Pro Phe Asp Val Asp Tyr
305                 310                 315                 320 cag caa acc ctt ggc tct cca ttc att tct ttc att gaa ctt tcc atg     1008
Gln Gln Thr Leu Gly Ser Pro Phe Ile Ser Phe Ile Glu Leu Ser Met
                325                 330                 335 att aat gaa cac tac aaa tgc aaa gag aac tgc aat cca gct aag tcg     1056
Ile Asn Glu His Tyr Lys Cys Lys Glu Asn Cys Asn Pro Ala Lys Ser
            340                 345                 350 gct aaa tgc gaa atg ggc gga ttc cct cat ccc cga gac tgc agc aaa     1104
Ala Lys Cys Glu Met Gly Gly Phe Pro His Pro Arg Asp Cys Ser Lys
        355                 360                 365 tgt atc tgt cct ggt gga tac gcc gga gct cga tgc acc gaa aga cca     1152
Cys Ile Cys Pro Gly Gly Tyr Ala Gly Ala Arg Cys Thr Glu Arg Pro
370                 375                 380 tca ggg tgt ggc agt gca att caa gct tcg tcc gat tgg aag acc tta     1200
Ser Gly Cys Gly Ser Ala Ile Gln Ala Ser Ser Asp Trp Lys Thr Leu
385                 390                 395                 400 caa gat acc ctt ggc aag gat gat gat gaa gaa cga gag gac ttc gag     1248
Gln Asp Thr Leu Gly Lys Asp Asp Asp Glu Glu Arg Glu Asp Phe Glu
                405                 410                 415 aca tgt aat tac tgg att gaa tct cct gcc gga acm gaa atc gaa gtg     1296
Thr Cys Asn Tyr Trp Ile Glu Ser Pro Ala Gly Xaa Glu Ile Glu Val
            420                 425                 430 agg tta ttg gat ttc acg agg ggt gtt tct gtc gat gga tgc aaa ttt     1344
Arg Leu Leu Asp Phe Thr Arg Gly Val Ser Val Asp Gly Cys Lys Phe
        435                 440                 445 gcc ggt gta gag atc aag acc aat aag gat caa aca ctc act ggc tac     1392
Ala Gly Val Glu Ile Lys Thr Asn Lys Asp Gln Thr Leu Thr Gly Tyr
450                 455                 460 agg ttc tgc aca gct ggc gca gct ggc ata gca ctt cgt tct tac acg     1440
Arg Phe Cys Thr Ala Gly Ala Ala Gly Ile Ala Leu Arg Ser Tyr Thr
465                 470                 475                 480 aat cgc gtc cca ata atg aca tac aac aga ttt ggt caa tcg acg act     1488
Asn Arg Val Pro Ile Met Thr Tyr Asn Arg Phe Gly Gln Ser Thr Thr
                485                 490                 495 gtt ctc gaa tac cga cac gtt ccg gcg agt gcg cca aga acg ccc tca     1536
Val Leu Glu Tyr Arg His Val Pro Ala Ser Ala Pro Arg Thr Pro Ser
            500                 505                 510 cct cca tct gct aca act cgt gct tct att act act act act acg         1584
Pro Pro Ser Ala Thr Thr Arg Ala Ser Ile Thr Thr Thr Thr Thr
        515                 520                 525 aag aaa ccc agc tct act gct gcc ttt aaa tgc gag gac aac cac act     1632
Lys Lys Pro Ser Ser Thr Ala Ala Phe Lys Cys Glu Asp Asn His Thr
530                 535                 540 tgt ccc tca ctt gta gcg agc ggt ttc tgc aaa ggg cca ctc tca gag     1680
Cys Pro Ser Leu Val Ala Ser Gly Phe Cys Lys Gly Pro Leu Ser Glu
545                 550                 555                 560 gct acc aag aag aaa gtg tgt cca aag tcg tgt gga ctc tgc tga         1725
Ala Thr Lys Lys Lys Val Cys Pro Lys Ser Cys Gly Leu Cys
                565                 570 tacaacactt tctctgtaat aaaatctgaa caattc                             1761
```

<210> SEQ ID NO 14
<211> LENGTH: 574
<212> TYPE: PRT
<213> ORGANISM: Ostertagia ostertagi
<220> FEATURE:
<221> NAME/KEY: misc_feature
<222> LOCATION: (83)..(83)

```
<223> OTHER INFORMATION: The xaa at location 83 stands for Glu, Ala, or
      Ser.
<220> FEATURE:
<221> NAME/KEY: misc_feature
<222> LOCATION: (86)..(86)
<223> OTHER INFORMATION: The xaa at location 86 stands for Glu, Val,
      Lys, or Met.
<220> FEATURE:
<221> NAME/KEY: misc_feature
<222> LOCATION: (87)..(87)
<223> OTHER INFORMATION: The xaa at location 87 stands for Lys, or Asn.
<220> FEATURE:
<221> NAME/KEY: misc_feature
<222> LOCATION: (88)..(88)
<223> OTHER INFORMATION: The xaa at location 88 stands for Trp, or Ser.
<220> FEATURE:
<221> NAME/KEY: misc_feature
<222> LOCATION: (90)..(90)
<223> OTHER INFORMATION: The xaa at location 90 stands for Pro.
<220> FEATURE:
<221> NAME/KEY: misc_feature
<222> LOCATION: (91)..(91)
<223> OTHER INFORMATION: The xaa at location 91 stands for Pro, or Ser.
<220> FEATURE:
<221> NAME/KEY: misc_feature
<222> LOCATION: (92)..(92)
<223> OTHER INFORMATION: The xaa at location 92 stands for Glu, Ala,
      Lys, or Thr.
<220> FEATURE:
<221> NAME/KEY: misc_feature
<222> LOCATION: (93)..(93)
<223> OTHER INFORMATION: The xaa at location 93 stands for Gly, Glu, or
      Asp.
<220> FEATURE:
<221> NAME/KEY: misc_feature
<222> LOCATION: (95)..(95)
<223> OTHER INFORMATION: The xaa at location 95 stands for Gln, Pro,
      or Ser.
<220> FEATURE:
<221> NAME/KEY: misc_feature
<222> LOCATION: (96)..(96)
<223> OTHER INFORMATION: The xaa at location 96 stands for Ser, Asn,
      Cys, or Tyr.
<220> FEATURE:
<221> NAME/KEY: misc_feature
<222> LOCATION: (97)..(97)
<223> OTHER INFORMATION: The xaa at location 97 stands for Gly, Ala,
      Arg, or Thr.
<220> FEATURE:
<221> NAME/KEY: misc_feature
<222> LOCATION: (98)..(98)
<223> OTHER INFORMATION: The xaa at location 98 stands for Arg.
<220> FEATURE:
<221> NAME/KEY: misc_feature
<222> LOCATION: (99)..(99)
<223> OTHER INFORMATION: The xaa at location 99 stands for Asp, or Ala.
<220> FEATURE:
<221> NAME/KEY: misc_feature
<222> LOCATION: (100)..(100)
<223> OTHER INFORMATION: The xaa at location 100 stands for Gly, Ala,
      Arg, or Pro.
<220> FEATURE:
<221> NAME/KEY: misc_feature
<222> LOCATION: (102)..(102)
<223> OTHER INFORMATION: The xaa at location 102 stands for Arg, or His.
<220> FEATURE:
<221> NAME/KEY: misc_feature
<222> LOCATION: (103)..(103)
<223> OTHER INFORMATION: The xaa at location 103 stands for Val.
<220> FEATURE:
<221> NAME/KEY: misc_feature
<222> LOCATION: (104)..(104)
<223> OTHER INFORMATION: The xaa at location 104 stands for Gly, Val, or
      Leu.
<220> FEATURE:
<221> NAME/KEY: misc_feature
<222> LOCATION: (105)..(105)
<223> OTHER INFORMATION: The xaa at location 105 stands for Arg, or Cys.
<220> FEATURE:
```

```
<221> NAME/KEY: misc_feature
<222> LOCATION: (106)..(106)
<223> OTHER INFORMATION: The xaa at location 106 stands for Glu, or Lys.
<220> FEATURE:
<221> NAME/KEY: misc_feature
<222> LOCATION: (108)..(108)
<223> OTHER INFORMATION: The xaa at location 108 stands for Ser, or Asn.
<220> FEATURE:
<221> NAME/KEY: misc_feature
<222> LOCATION: (428)..(428)
<223> OTHER INFORMATION: The xaa at location 428 stands for Thr.

<400> SEQUENCE: 14
```

| | | | | | | | | | | | | | | |
|---|---|---|---|---|---|---|---|---|---|---|---|---|---|---|
| Met | Arg | Leu | Ile | Leu | Leu | Ile | Leu | Leu | Val | Val | Ala | Thr | Asn | Gly |
| 1 | | | | 5 | | | | | 10 | | | | | 15 |
| Gly | Ile | Ile | Asp | Lys | Leu | Lys | Gly | Leu | Phe | Thr | Gly | Glu | Gly | Phe |
| | | | | 20 | | | | | 25 | | | | | 30 |
| Gly | Gln | Lys | Val | Lys | Asn | Ala | Thr | Ala | Val | Gly | Phe | Lys | Lys | Leu | Phe |
| | | | 35 | | | | | 40 | | | | | 45 | | |
| Glu | Asn | Thr | Ala | Leu | Phe | Arg | Ile | Asn | Asp | Lys | Ile | Arg | Ser | Met | Lys |
| | 50 | | | | | 55 | | | | | 60 | | | | |
| Glu | Lys | Val | Leu | Lys | Thr | Leu | Glu | Leu | Ser | Pro | Ala | Met | Met | Lys | Ser |
| 65 | | | | | 70 | | | | | 75 | | | | | 80 |
| Leu | Gln | Xaa | Arg | Leu | Xaa | Xaa | Xaa | Arg | Xaa | Xaa | Xaa | Xaa | Arg | Xaa | Xaa |
| | | | | 85 | | | | | 90 | | | | | 95 | |
| Xaa | Xaa | Xaa | Xaa | Arg | Xaa | Xaa | Xaa | Xaa | Val | Xaa | Lys | Asn | Ser | Glu |
| | | | 100 | | | | | 105 | | | | | 110 | |
| Val | Asp | Gln | Tyr | Leu | Tyr | Gln | Gly | Asp | Met | Val | Leu | Thr | Glu | Glu | Gln |
| | | | 115 | | | | | 120 | | | | | 125 | | |
| Ala | Asp | Glu | Ile | Val | Glu | Asp | Ile | Glu | Asp | Gln | Val | Ala | Gly | Gly | Asn |
| | 130 | | | | | 135 | | | | | 140 | | | | |
| Arg | Thr | Lys | Arg | Gln | Ala | Phe | Lys | Asp | His | Lys | Tyr | Pro | Lys | Thr | Leu |
| 145 | | | | | 150 | | | | | 155 | | | | | 160 |
| Trp | Ser | Gln | Gly | Val | Asn | Tyr | Tyr | Phe | His | Asp | Met | Ala | Ser | Lys | Gln |
| | | | | 165 | | | | | 170 | | | | | 175 | |
| Met | Lys | Ser | Val | Phe | Val | Lys | Gly | Ala | Lys | Trp | Trp | Glu | Lys | Asp | Thr |
| | | | 180 | | | | | 185 | | | | | 190 | | |
| Cys | Ile | Asn | Phe | Thr | Glu | Asn | Arg | Ser | Ala | Glu | Asp | Arg | Ile | Met | Val |
| | | | | 195 | | | | | 200 | | | | | 205 | |
| Phe | Pro | Gln | Lys | Gly | Cys | Trp | Ser | Asn | Ile | Gly | Lys | Ile | Gly | Gly | Glu |
| | | | 210 | | | | | 215 | | | | | 220 | | |
| Gln | Lys | Ile | Ser | Leu | Gly | Gly | Gly | Cys | His | Ser | Val | Ser | Ile | Ala | Ala |
| 225 | | | | | 230 | | | | | 235 | | | | | 240 |
| His | Glu | Ile | Gly | His | Ala | Ile | Gly | Phe | Phe | His | Thr | Met | Ser | Arg | His |
| | | | | 245 | | | | | 250 | | | | | 255 | |
| Asp | Arg | Asp | Glu | Phe | Ile | Thr | Val | Asn | Met | His | Asn | Val | Asp | Val | His |
| | | | 260 | | | | | 265 | | | | | 270 | | |
| Trp | Leu | Ser | Gln | Phe | Asn | Lys | Glu | Thr | Thr | Lys | Arg | Asn | Asp | Asn | Tyr |
| | | 275 | | | | | 280 | | | | | 285 | | | |
| Gly | Met | Thr | Tyr | Asp | Tyr | Gly | Ser | Ile | Met | His | Tyr | Gly | Gly | Thr | Ser |
| | 290 | | | | | 295 | | | | | 300 | | | | |
| Ala | Ser | Tyr | Asn | Asn | Lys | Pro | Thr | Met | Val | Pro | Phe | Asp | Val | Asp | Tyr |
| 305 | | | | | 310 | | | | | 315 | | | | | 320 |
| Gln | Gln | Thr | Leu | Gly | Ser | Pro | Phe | Ile | Ser | Phe | Ile | Glu | Leu | Ser | Met |
| | | | | 325 | | | | | 330 | | | | | 335 | |
| Ile | Asn | Glu | His | Tyr | Lys | Cys | Lys | Glu | Asn | Cys | Asn | Pro | Ala | Lys | Ser |
| | | | 340 | | | | | 345 | | | | | 350 | | |

```
Ala Lys Cys Glu Met Gly Gly Phe Pro His Pro Arg Asp Cys Ser Lys
        355                 360                 365

Cys Ile Cys Pro Gly Gly Tyr Ala Gly Ala Arg Cys Thr Glu Arg Pro
        370                 375                 380

Ser Gly Cys Gly Ser Ala Ile Gln Ala Ser Ser Asp Trp Lys Thr Leu
385                 390                 395                 400

Gln Asp Thr Leu Gly Lys Asp Asp Glu Glu Arg Glu Asp Phe Glu
                405                 410                 415

Thr Cys Asn Tyr Trp Ile Glu Ser Pro Ala Gly Xaa Glu Ile Glu Val
        420                 425                 430

Arg Leu Leu Asp Phe Thr Arg Gly Val Ser Val Asp Gly Cys Lys Phe
        435                 440                 445

Ala Gly Val Glu Ile Lys Thr Asn Lys Asp Gln Thr Leu Thr Gly Tyr
        450                 455                 460

Arg Phe Cys Thr Ala Gly Ala Gly Ile Ala Leu Arg Ser Tyr Thr
465                 470                 475                 480

Asn Arg Val Pro Ile Met Thr Tyr Asn Arg Phe Gly Gln Ser Thr Thr
                485                 490                 495

Val Leu Glu Tyr Arg His Val Pro Ala Ser Ala Pro Arg Thr Pro Ser
                500                 505                 510

Pro Pro Ser Ala Thr Thr Arg Ala Ser Ile Thr Thr Thr Thr Thr
        515                 520                 525

Lys Lys Pro Ser Ser Thr Ala Ala Phe Lys Cys Glu Asp Asn His Thr
        530                 535                 540

Cys Pro Ser Leu Val Ala Ser Gly Phe Cys Lys Gly Pro Leu Ser Glu
545                 550                 555                 560

Ala Thr Lys Lys Lys Val Cys Pro Lys Ser Cys Gly Leu Cys
                565                 570

<210> SEQ ID NO 15
<211> LENGTH: 24
<212> TYPE: DNA
<213> ORGANISM: Artificial
<220> FEATURE:
<223> OTHER INFORMATION: primer: Lambdagt11F
<220> FEATURE:
<221> NAME/KEY: misc_feature
<223> OTHER INFORMATION: Lambdagt11F

<400> SEQUENCE: 15
ggtggcgacg actcctggag cccg                                                24

<210> SEQ ID NO 16
<211> LENGTH: 24
<212> TYPE: DNA
<213> ORGANISM: Artificial
<220> FEATURE:
<223> OTHER INFORMATION: primer: Lambdagt11R

<400> SEQUENCE: 16
ttgacaccag accaactggt aatg                                                24

<210> SEQ ID NO 17
<211> LENGTH: 20
<212> TYPE: DNA
<213> ORGANISM: Artificial
<220> FEATURE:
<223> OTHER INFORMATION: primer: SP6

<400> SEQUENCE: 17
```

```
atttaggtga cactatagaa                                                    20

<210> SEQ ID NO 18
<211> LENGTH: 22
<212> TYPE: DNA
<213> ORGANISM: Artificial
<220> FEATURE:
<223> OTHER INFORMATION: primer: T7

<400> SEQUENCE: 18
gtaatacgac tcactatagg gc                                                 22

<210> SEQ ID NO 19
<211> LENGTH: 21
<212> TYPE: DNA
<213> ORGANISM: Artificial
<220> FEATURE:
<223> OTHER INFORMATION: primer: 24kForw

<400> SEQUENCE: 19
gaattcatga agttggtcgt g                                                  21

<210> SEQ ID NO 20
<211> LENGTH: 22
<212> TYPE: DNA
<213> ORGANISM: Artificial
<220> FEATURE:
<223> OTHER INFORMATION: primer: 24kRev

<400> SEQUENCE: 20
ctcgagtcaa tagatccttg tg                                                 22

<210> SEQ ID NO 21
<211> LENGTH: 36
<212> TYPE: DNA
<213> ORGANISM: Artificial
<220> FEATURE:
<223> OTHER INFORMATION: primer: AAP
<220> FEATURE:
<221> NAME/KEY: misc_feature
<222> LOCATION: (24)..(25)
<223> OTHER INFORMATION: n = Inosine
<220> FEATURE:
<221> NAME/KEY: misc_feature
<222> LOCATION: (29)..(30)
<223> OTHER INFORMATION: n = Inosine
<220> FEATURE:
<221> NAME/KEY: misc_feature
<222> LOCATION: (34)..(35)
<223> OTHER INFORMATION: n = Inosine

<400> SEQUENCE: 21
ggccacgcgt cgactagtac gggnngggnn gggnng                                  36

<210> SEQ ID NO 22
<211> LENGTH: 32
<212> TYPE: DNA
<213> ORGANISM: Artificial
<220> FEATURE:
<223> OTHER INFORMATION: primer: UAP

<400> SEQUENCE: 22
cuacuacuac uaggccacgc gtcgactagt ac                                      32

<210> SEQ ID NO 23
<211> LENGTH: 21
<212> TYPE: DNA
```

```
<213> ORGANISM: Artificial
<220> FEATURE:
<223> OTHER INFORMATION: primer: 65Rev1

<400> SEQUENCE: 23
cagcaatgga taccgaatga c                                            21

<210> SEQ ID NO 24
<211> LENGTH: 22
<212> TYPE: DNA
<213> ORGANISM: Artificial
<220> FEATURE:
<223> OTHER INFORMATION: primer: 65Rev2

<400> SEQUENCE: 24
agtgacttca tcattgctgg tg                                           22

<210> SEQ ID NO 25
<211> LENGTH: 21
<212> TYPE: DNA
<213> ORGANISM: Artificial
<220> FEATURE:
<223> OTHER INFORMATION: primer: 65kForw

<400> SEQUENCE: 25
tgatgatgaa gaacgagagg a                                            21

<210> SEQ ID NO 26
<211> LENGTH: 30
<212> TYPE: DNA
<213> ORGANISM: Artificial
<220> FEATURE:
<223> OTHER INFORMATION: primer: For65

<400> SEQUENCE: 26
ggatccatga ggctgatatt gctcatttta                                   30

<210> SEQ ID NO 27
<211> LENGTH: 27
<212> TYPE: DNA
<213> ORGANISM: Artificial
<220> FEATURE:
<223> OTHER INFORMATION: primer: Rev65

<400> SEQUENCE: 27
ctcgaggcag agtccacacg actttgg                                      27
```